United States Patent [19]

Herold et al.

[11] Patent Number: 4,898,977

[45] Date of Patent: Feb. 6, 1990

[54] PROCESSES FOR THE PREPARATION OF 5-AMINO-4-HYDROXYVALERIC ACID DERIVATIVES

[75] Inventors: Peter Herold, Basel, Switzerland; Christof Angst, Summit, N.J.

[73] Assignee: Ciba-Geigy Corporation, Ardsley, N.Y.

[21] Appl. No.: 85,437

[22] Filed: Aug. 13, 1987

[30] Foreign Application Priority Data

Aug. 13, 1986 [CH] Switzerland .................. 3248/86

[51] Int. Cl.⁴ .......................................... C07C 103/19
[52] U.S. Cl. ...................... 564/191; 544/130; 544/132; 544/139; 544/159; 544/162; 544/163; 544/168; 544/171; 544/175; 544/176; 546/14; 546/208; 546/210; 546/226; 546/233; 546/230; 546/235; 548/342; 548/495; 548/540; 548/568; 548/573; 549/321; 549/323; 549/324; 556/416; 556/418; 556/419; 558/254; 558/255; 558/404; 558/406; 558/436; 558/437; 558/438; 558/441; 558/445; 560/12; 560/16; 560/29; 560/34; 560/35; 560/39; 560/118; 560/120; 560/121; 560/125; 560/126; 560/147; 560/148; 560/150; 560/153; 560/168; 560/169; 560/170; 560/312; 562/426; 562/430; 562/439; 562/440; 562/444; 562/448; 562/503; 562/507; 562/508; 562/556; 562/560; 562/564; 562/567; 564/144; 564/133; 564/162; 564/165; 564/189; 564/197; 564/198; 564/204; 564/205; 552/10; 552/12

[58] Field of Search .............. 562/567, 430, 426, 439, 562/440, 444, 448, 507, 564, 556, 560; 546/14, 210, 208, 226, 230, 233, 235; 560/12, 29, 16, 34, 35, 39, 118, 120, 125, 147, 148, 150, 153, 168, 169, 170; 544/130, 139, 132, 159, 163, 162, 168, 175, 176, 171; 564/144, 197, 198, 133, 194, 189, 191, 162, 165; 556/416, 418, 419; 558/404, 406, 436, 437, 438, 441, 445, 254, 255; 548/342, 495, 540, 568, 573

[56] References Cited

U.S. PATENT DOCUMENTS

4,031,115  6/1977  Kurkov ........................... 260/343.6
4,487,963  12/1984  Bock ................................ 562/567

FOREIGN PATENT DOCUMENTS

206090  12/1986  European Pat. Off. .
270234  6/1988  European Pat. Off. .
1914380  10/1970  Fed. Rep. of Germany .

OTHER PUBLICATIONS

Dowle et al., Chem. Society Reviews, vol. 8, p. 171 (1979).
Herold et al., J. Org. Chem. vol. 54, p. 1178 (1989).

Primary Examiner—Michael L. Shippen
Attorney, Agent, or Firm—JoAnn Villamizar; Irving M. Fishman

[57] ABSTRACT

The invention relates to novel processes and intermediates for the preparation of 5-amino-4-hydroxyvaleric acid derivatives of the formula

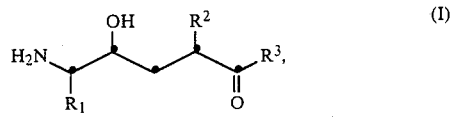

in which $R^1$ represents hydrogen, optionally substituted alkyl, cycloalkyl, cycloalkyl-lower alkyl, aryl, aryl-lower alkyl or the radical of a natural amino acid, $R^2$ represents hydrogen, optionally substituted alkyl, cycloalkyl, cycloalkyl-lower alkyl, aryl, aryl-lower alkyl, amino, hydroxy, mercapto, sulphinyl, sulphonyl or the radical of a natural amino acid, and $R^3$ represents optionally substituted hydroxy or amino, by sigmatropic rearrangement of a suitable allyl ester, halolactonisation of the resulting $\gamma,\delta$-unsaturated acid or of a suitable derivative thereof, exchange of halogen for a nitrogen-containing nucleophile, opening of the lactone ring and freeing of the amino group. Compounds of the formula I are starting materials for the preparation of renin-inhibitors which have an anti-hypertensive action.

6 Claims, No Drawings

PROCESSES FOR THE PREPARATION OF 5-AMINO-4-HYDROXYVALERIC ACID DERIVATIVES

The invention relates to novel processes for the preparation of 5-amino-4-hydroxyvaleric acid derivatives which can be used as starting materials for the preparation of renin-inhibitors which have an anti-hypertensive action and for the preparation of other pharmaceuticals. The invention relates also to novel intermediates.

The 5-amino-4-hydroxyvaleric acid derivatives that can be prepared by the processes according to the invention are mimetics for a dipeptide unit. In place of the central amide function, the mimetics contain a hydroxyethylene group. These mimetics can be incorporated into polypeptides or polypeptide-like compounds. Polypeptides or polypeptide-like compounds that have been modified in that manner generally exhibit physiological properties similar to those of corresponding unmodified polypeptides. Since a central amide bond has been replaced by a hydroxyethylene group, however, they are stable towards hydrolytic cleavage at that central bond and therefore acquire additional properties which may be advantageous, such as prolonged activity in the natural, physiological environment owing to their stability towards proteases, and/or irreversible bonding to enzymes that would cleave the central amide bond.

The preparation of 5-amino-4-hydroxyvaleric acid derivatives has already been described in European Patent Application 143 746. Compared with the previously known process, the novel processes constitute a substantial improvement in that they allow the preparation of 5-amino-4-hydroxyvaleric acid derivatives in higher overall yields, with higher stereoselectivity and with less complicated purification methods.

The invention relates to processes for the preparation of compounds of the formula

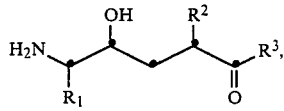
(I)

in which $R_1$ represents hydrogen, optionally substituted alkyl, cycloalkyl, cycloalkyl-lower alkyl, aryl, aryl-lower alkyl or the radical of a natural amino acid, $R^2$ represents hydrogen, optionally substituted alkyl, cycloalkyl, cycloalkyl-lower alkyl, aryl, aryl-lower alkyl, amino, hydroxy, mercapto, sulphinyl, sulphonyl or the radical of a natural amino acid, and $R^3$ represents optionally substituted hydroxy or amino, and of salts of these compounds, characterised in that an allyl alcohol of the formula

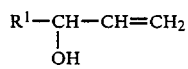
(II)

is esterified with an acid or ester of the formula

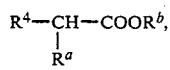
(III)

in which $R^a$ represents hydrogen or a group $COOR^b$ and $R^b$ represents hydrogen, a hydrocarbon radical or a silyl radical, and $R^4$ has the meanings of $R^2$ or is halogen, or with a derivative thereof, in the presence of a catalyst, the resulting compound is, in situ and/or after treatment with a base and a silylating agent, rearranged by heating and optionally decarboxylated, the resulting compound of the formula

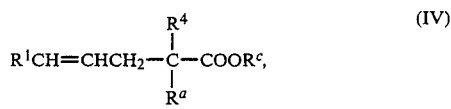
(IV)

in which $R^c$ represents hydrogen, a hydrocarbon radical or a silyl radical, is hydrolysed if $R^c$ is other than hydrogen and/or $R^a$ represents a group $COOR^b$ and $R^b$ is other than hydrogen, and decarboxylated if $R^a$ represents a group $COOR^b$, and, if $R^4$ represents halogen, halogen is exchanged for amino, hydroxy or mercapto, a resulting compound of the formula

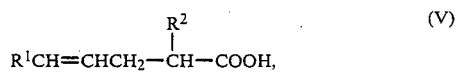
(V)

if desired after separating the enantiomers and/or converting the carboxy group into a carboxamide function or into a hydroxamic acid ester group, is halolactonised with a halogenating agent, in a resulting compound of the formula

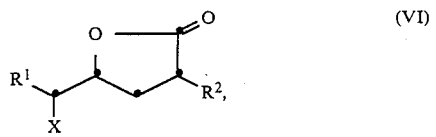
(VI)

in which X represents halogen, halogen is exchanged for a radical bonded by way of nitrogen and, in any desired sequence, the lactone ring is opened with a compound that introduces the radical $R^3$, and the nitrogen-containing radical X is converted into an amino group and the latter is optionally protected, and, in a resulting compound, any protecting groups that may be present are removed and/or, if desired, a resulting compound of the formula I is converted into its salt or a resulting salt is converted into the free compound and/or, if desired, resulting mixtures of isomers are separated.

In the description of the present invention, the term "lower" used in the definition of groups and radicals, for example lower alkyl, lower alkoxy, lower alkanoyl, etc., means that the groups or radicals so designated, unless expressly defined otherwise, contain from 1 to 7 C-atoms and preferably from 1 to 4 C-atoms.

The C-atoms that are substituted by four different radicals, for example the C-atoms of a compound of the formula I carrying the radicals $R^1$, OH and $R^2$, the C-atom of a compound of the formula II carrying the radical $R^1$, the C-atoms of compounds of the formulae IV and V carrying the radical $R^2$ or $R^4$, and the C-atoms of a compound of the formula VI carrying the radicals $R^1$, —OCO and $R^2$, may have the R-, S- or R,S-configuration.

The general terms and expressions used in the definition of substituents have preferably the following meanings:

Alkyl $R^1$, $R^2$ or $R^4$ preferably has up to 12 C-atoms and is lower alkyl having from 1 to 7 C-atoms or, for example, n-octyl, n-nonyl, n-decyl or n-dodecyl. Lower alkyl $R^1$, $R^2$ or $R^4$ is, for example, methyl, ethyl, n-propyl, isopropyl, n-butyl, sec.-butyl, isobutyl, n-pentyl, isopentyl or n-hexyl. Alkyl $R^1$, $R^2$ or $R^4$ may be substituted by one or more functional groups, for example by hydroxy, etherified hydroxy, for example lower alkoxy, such as methoxy or ethoxy, esterified hydroxy, for example lower alkanoyloxy, such as acetoxy, halogen, for example fluorine or chlorine, carboxy, esterified carboxy, for example lower alkoxycarbonyl, such as methoxycarbonyl or ethoxycarbonyl, amidated carboxy, for example carbamoyl or mono- or di-lower alkylcarbamoyl, such as mono- or di-methylcarbamoyl, cyano, amino, mono- or di-lower alkylamino, for example methylamino or dimethylamino, cyclic substituted amino, for example pyrrolidino, piperidino or morpholino, or by oxo.

Cycloalkyl $R^1$, $R^2$ or $R^4$ is mono-, bi- or tri-cyclic and is optionally substituted by one or more of the functional groups mentioned under alkyl $R^1$. Monocyclic cycloalkyl contains, for example, from 3 to 8, especially from 5 to 7, C-atoms and is, for example, cyclopropyl, cyclopentyl, cyclohexyl or cycloheptyl. Bicyclic cycloalkyl contains, for example, from 6 to 10 C-atoms and is, for example, endo- or exo-norbornyl or α- or β-decahydronaphthyl. Tricyclic cycloalkyl contains, for example, from 8 to 10 C-atoms and is, for example, 1-adamantyl.

Cycloalkyl-lower alkyl $R^1$, $R^2$ or $R^4$ is a lower alkyl radical as defined above under alkyl $R^1$ which carries one or more mono-, bi- or tri-cyclic cycloalkyl groups and is optionally substituted by further radicals from among those mentioned above. In particular, cycloalkyl-lower alkyl contains from 6 to 10 C-atoms and is, for example, lower alkyl having from 1 to 4 C-atoms which carries a cyclopentyl, cyclohexyl or cycloheptyl group, for example cyclopentylmethyl, cyclohexylmethyl, 2-cyclohexylethyl or cycloheptylmethyl.

Aryl $R^1$, $R^2$ or $R^4$ preferably contains from 6 to 14 C-atoms and is, for example, phenyl or 1- or 2-naphthyl unsubstituted or substituted by one or more functional groups, for example by lower alkyl, for example methyl, hydroxy, etherified hydroxy, for example lower alkoxy, such as methoxy, esterified hydroxy, for example lower alkanoyloxy, such as acetoxy, amino, lower alkylamino, for example methylamino, di-lower alkylamino, for example dimethylamino, acylamino, for example tert.-butoxycarbonylamino, or by halo, for example fluorine, chlorine, bromine or iodine, it being possible for the substituent(s) to be in any position of the aryl radical, for example in the o-, m- or p-position of the phenyl radical.

Aryl-lower alkyl $R^1$, $R^2$ or $R^4$ contains, for example, from 7 to 20 C-atoms and is, for example, a lower alkyl radical as defined above under alkyl $R^1$ which carries one or more of the aryl radicals defined above and is optionally substituted by further functional groups from among those mentioned above. For example, aryl-lower alkyl contains from 7 to 11 C-atoms and is, for example, lower alkyl having from 1 to 4 C-atoms that carries an unsubstituted phenyl group or a phenyl group substituted by lower alkyl, hydroxy, lower alkoxy or by halo, or an α- or β-naphthyl group, for example benzyl, 4-methylbenzyl, 4-hydroxybenzyl, 2-phenethyl or α- or β-naphthylmethyl.

A radical of a natural amino acid $R^1$, $R^2$ or $R^4$ is a radical as is linked in natural α-amino acids to the α-C-atom. Natural α-amino acids are those which usually occur in proteins, for example glycine, alanine, valine, norvaline, leucine, isoleucine, norleucine, serine, homoserine, threonine, methionine, cysteine, phenylalanine, tyrosine, tryptophan, aspartic acid, asparagine, glutamic acid, glutamine, histidine, arginine, lysine, ornithine, α,γ-diaminobutyric acid and α,β-diaminopropionic acid. Radicals of such amino acids are in some cases already included under one of the definitions given above and are especially hydrogen, methyl, isopropyl, n-propyl, isobutyl, sec.-butyl, n-butyl, hydroxymethyl, 2-hydroxyethyl, 1-hydroxyethyl, 2-methylthioethyl, mercaptomethyl, benzyl, 4-hydroxybenzyl, 3-indolylmethyl, carboxymethyl, carbamoylmethyl, 2-carboxyethyl, 2-carbamoylethyl, 4-imidazolylmethyl, 3-guanidinopropyl, 4-aminobutyl, 2-aminoethyl and aminomethyl.

Amino $R^2$ or $R^4$ is optionally substituted, for example, by one or two lower alkyl groups, by aryl-lower alkyl, lower alkanoyl, lower alkoxycarbonyl or by aryl-lower alkoxycarbonyl, or is part of a ring and is, for example, amino, methylamino, ethylamino, n-butylamino, dimethylamino, benzylamino, acetylamino, pivaloylamino, methoxy-, ethoxy- or tert.-butoxycarbonylamino, benzyloxycarbonylamino, pyrrolidino, piperidino or morpholino.

Hydroxy $R^2$ or $R^4$ is optionally substituted, for example, by unsubstituted or substituted lower alkyl, for example lower alkanoyloxy-lower alkyl or lower alkoxycarbonyloxy-lower alkyl, aryl, aryl-lower alkyl, lower alkanoyl, cycloalkylcarbonyl, arylcarbonyl or by silyl, for example tri-lower alkylsilyl, and is, for example, hydroxy, methoxy, ethoxy, acetoxymethoxy, tert.-butoxycarbonyloxymethoxy, phenoxy, benzyloxy, acetoxy, pivaloyloxy, cyclohexylcarbonyloxy, benzoyloxy, trimethylsilyloxy or tert.-butyldimethylsilyloxy.

Mercapto $R^2$ or $R^4$ is optionally substituted, for example, by unsubstituted or substituted lower alkyl, for example hydroxy-lower alkyl, aryl, aryl-lower alkyl or by lower alkanoyl, and is, for example, mercapto, methylthio, ethylthio, isopropylthio, tert.-butylthio, 2-hydroxyethylthio, phenylthio, benzylthio or acetylthio.

Sulphinyl $R^2$ or $R^4$ is substituted, for example by unsubstituted or substituted lower alkyl, for example hydroxy-lower alkyl, aryl or by aryl-lower alkyl, and is, for example, methylsulphinyl, ethylsulphinyl, isopropylsulphinyl, tert.-butylsulphinyl, 2-hydroxyethylsulphinyl, phenylsulphinyl or benzylsulphinyl. The sulphur atom in sulphinyl may be in the R-, S- or R,S-configuration.

Sulphonyl $R^2$ or $R^4$ is substituted, for example by unsubstituted or substituted lower alkyl, for example hydroxy-lower alkyl, aryl or by aryl-lower alkyl, and is, for example, methylsulphonyl, ethylsulphonyl, isopropylsulphonyl, tert.-butylsulphonyl, 2-hydroxyethylsulphonyl, phenylsulphonyl or benzylsulphonyl.

Optionally substituted hydroxy $R^3$ is unsubstituted or substituted by an unsubstituted or substituted, saturated or unsaturated aliphatic, aromatic, heteroaromatic, aromatic-aliphatic or heteroaromatic-aliphatic hydrocarbon radical having up to 18, preferably having up to 10, C-atoms Optionally substituted amino $R^3$ is unsubstituted or substituted by one or two unsubstituted or substituted, saturated or unsaturated aliphatic, aromatic, heteroaromatic, aromatic-aliphatic or heteroaromatic-aliphatic hydrocarbon radicals having up to 18, preferably having up to 10, C-atoms, or is part of a nitrogen-containing ring.

An unsubstituted or substituted, saturated or unsaturated aliphatic hydrocarbon radical is, for example, optionally substituted alkyl having up to 12 C-atoms, mono-, bi- or tri-cyclic cycloalkyl or cycloalkyl-lower alkyl, as defined above for the radicals $R^1$, $R^2$ and $R^4$, or also lower alkenyl having from 2 to 7 C-atoms or lower alkynyl having from 2 to 7 C-atoms, it being possible for these radicals to be substituted by the functional groups mentioned under alkyl $R^1$, for example vinyl, allyl, 2- or 3-butenyl, 3-carboxy-2-propenyl or 2-propynyl.

An unsubstituted or substituted aromatic or aromatic-aliphatic hydrocarbon radical is, for example, optionally substituted aryl having from 6 to 14 C-atoms or aryl-lower alkyl having from 7 to 20 C-atoms, as defined above for the radicals $R^1$, $R^2$ and $R^4$.

An unsubstituted or substituted heteroaromatic hydrocarbon radical is, for example, a mono-, bi- or tricyclic heterocycle containing one or two nitrogen atoms and/or an oxygen or sulphur atom, for example pyrrolyl, furyl, thienyl, imidazolyl, pyrazolyl, oxazolyl, thiazolyl, pyridyl, pyrazinyl, pyrimidinyl, indolyl, quinolyl, isoquinolyl, quinoxalinyl or β-carbolinyl. This heterocycle may be substituted at a nitrogen atom by lower alkyl, for example methyl, phenyl, phenyl-lower alkyl, for example benzyl, and/or at one or more carbon atoms by lower alkyl, for example methyl, phenyl, halogen, for example chlorine, hydroxy, lower alkoxy, for example methoxy, phenyl-lower alkoxy, for example benzyloxy, or by oxo, and may be partially saturated, and is, for example, 2- or 3-pyrrolyl, 5-phenyl-2-pyrrolyl, 2-furyl, 2-thienyl, 4-imidazolyl, 2-, 3- or 4-pyridyl, 2-, 3- or 5-indolyl, 1-methyl-, 5-methyl-, 5-methoxy- or 5-chloro-2-indolyl, 1-benzyl-2- or -3-indolyl, 2-, 3- or 4-quinolyl, 4-hydroxy-2-quinolyl, 1-oxo-1,2-dihydro-3-isoquinolyl or 2-quinoxalinyl.

An unsubstituted or substituted heteroaromatic-aliphatic hydrocarbon radical contains, for example, a lower alkyl radical as defined above under alkyl $R^1$ which carries one or two of the heterocycles defined above and is optionally substituted at the lower alkyl radical by other functional groups from among those mentioned above, for example lower alkyl having from 1 to 4 C-atoms that carries a mono- or bi-cyclic heterocycle having one or two nitrogen atoms, for example 2- or 3-pyrrolylmethyl, 2-, 3- or 4-pyridylmethyl, 2-(2-, 3- or 4-pyridyl)-ethyl, 4-imidazolylmethyl, 2-(4-imidazolyl)-ethyl, 2- or 3-indolylmethyl, 2-(3-indolyl)-ethyl or 2-quinolylmethyl.

Substituted amino $R^3$ as part of a nitrogen-containing ring is, for example, part of a five-, six- or seven-membered ring that, in addition to C-atoms, optionally contains a further unsubstituted or substituted nitrogen atom, an oxygen atom or a sulphur atom. Examples of substituents of this further nitrogen atom are lower alkyl, for example methyl, phenyl, phenyl-lower alkyl, for example benzyl, acyl, for example lower alkanoyl, such as acetyl or pivaloyl, lower alkoxycarbonyl, such as tert.-butoxycarbonyl, or phenyl-lower alkoxycarbonyl, such as benzyloxycarbonyl. Amino $R^3$ substituted in that manner is, for example, pyrrolidino, piperidino, hexamethyleneamino, morpholino, thiomorpholino, 4-methyl-1-piperazinyl or 4-acetyl-1-piperazinyl.

Halogen $R^4$ is fluorine, chlorine, bromine or iodine, preferably chlorine or bromine.

The functional groups present in the substituents $R^1$, $R^2$, $R^3$ or $R^4$, for example carboxy, amino, hydroxy or mercapto, may be in protected form instead of in free form. Suitable protecting groups and the methods by which they are introduced and removed are described, for example, in standard works, such as in J. F. W. McOmie, "Protective Groups in Organic Chemistry", Plenum Press, London and New York 1973, in Th. W. Greene, "Protective Groups in Organic Synthesis", Wiley, New York 1981, in "The Peptides", volume 3 (edited by E. Gross and J. Meienhofer), Academic Press, London and New York 1981, and in "Methoden der organischen Chemie", Houben-Weyl, 4th edition, vol. 15/I, Georg Thieme Verlag, Stuttgart 1974.

A carboxy group is protected, for example, in the form of an ester group that is selectively cleavable under mild conditions. A carboxy group protected in esterified form is esterified especially by a lower alkyl group that is branched in the 1-position of the lower alkyl group or substituted by suitable substituents in the 1- or 2-position of the lower alkyl group. Examples of a protected carboxy group are tert.-lower alkoxycarbonyl, for example tert.-butoxycarbonyl, arylmethoxycarbonyl having one or two aryl radicals, for example benzyloxycarbonyl, 4-nitrobenzyloxycarbonyl or diphenylmethoxycarbonyl, 1-lower alkoxy-lower alkoxycarbonyl, for example methoxymethoxycarbonyl, 1-methoxyethoxycarbonyl or 1-ethoxyethoxycarbonyl, aroylmethoxycarbonyl, for example phenacyloxycarbonyl, 2-halo-lower alkoxycarbonyl, for example 2,2,2-trichloroethoxycarbonyl, 2-bromoethoxycarbonyl or 2-iodoethoxycarbonyl, and also 2-tri-lower alkylsilyl-lower alkoxycarbonyl, for example 2-trimethylsilylethoxycarbonyl.

An amino group can be protected, for example, in the form of an acylamino or arylmethylamino group. In a corresponding acylamino group, acyl is, for example, the acyl radical of an organic carboxylic acid having, for example, up to 18 carbon atoms, especially of a lower alkanecarboxylic acid optionally substituted, for example, by halogen or by aryl, of a benzoic acid optionally substituted, for example, by halogen, lower alkoxy or by nitro, or preferably of a carbonic acid semiester. Such acyl groups are, for example, lower alkanoyl, such as formyl, acetyl, propionyl or pivaloyl, halo-lower alkanoyl, for example 2-haloacetyl, such as 2-chloro-, 2-bromo-, 2-iodo-, 2,2,2-trifluoro- or 2,2,2-trichloro-acetyl, benzoyl optionally substituted, for example, by halogen, lower alkoxy or by nitro, for example benzoyl, 4-chlorobenzoyl, 4-methoxybenzoyl or 4-nitrobenzoyl, or lower alkoxycarbonyl branched in the 1-position of the lower alkyl radical or suitably substituted in the 1- or 2-position, for example tert.-lower alkoxycarbonyl, such as tert.-butoxycarbonyl, arylmethoxycarbonyl having one or two aryl radicals which are phenyl optionally mono- or poly-substituted, for example, by lower alkyl, for example tert.-lower alkyl, such as tert.-butyl, lower alkoxy, such as methoxy, hydroxy, halogen, such as chlorine, and/or by nitro, for example benzyloxycarbonyl, 4-nitrobenzyloxycarbonyl, diphenylmethoxycarbonyl or di-(4-methoxyphenyl)-methoxycarbonyl, aroylmethoxycarbonyl, for example phenacyloxycarbonyl, 2-halo-lower alkoxycarbonyl, for example 2,2,2-trichloroethoxycarbonyl, 2-bromoethoxycarbonyl or 2-iodoethoxycarbonyl, 2-tri-lower alkylsilyl-lower alkoxycarbonyl, for example 2-trimethylsilylethoxycarbonyl, or 2-triarylsilyl-lower alkoxycarbonyl, for example 2-triphenylsilylethoxycarbonyl. An arylmethylamino group is, for example, mono-, di- or especially tri-phenylmethylamino, for example benzyl-, diphenylmethyl- or trityl-amino.

A hydroxy group can be protected, for example, by an acyl group, for example halo-substituted, for example chloro-substituted, lower alkanoyl, for example 2,2-dichloroacetyl, or especially by an acyl radical of a carbonic acid semiester mentioned for protected amino groups. A preferred hydroxy-protecting group is, for example, 2,2,2-trichloroethoxycarbonyl, 4-nitrobenzyloxycarbonyl, diphenylmethoxycarbonyl or trityl. A hydroxy group can also be protected by tri-lower alkylsilyl, for example trimethylsilyl or dimethyl-tert.-butylsilyl, a readily removable alkyl group, such as tert.-lower alkyl, for example tert.-butyl, an oxa- or a thia-aliphatic or -cycloaliphatic hydrocarbon radical, for example 1-lower alkoxy-lower alkyl or 1-lower alkylthio-lower alkyl, for example methoxymethyl, 1-methoxyethyl, 1-ethoxyethyl, methylthiomethyl, 1-methylthioethyl or 1-ethylthioethyl, or 2-oxa- or 2-thia-cycloalkyl having from 5 to 7 ring atoms, for example 2-tetrahydrofuryl or 2-tetrahydropyranyl, or a corresponding thia analogue, or also by 1-phenyl-lower alkyl, for example benzyl, diphenylmethyl or trityl, it being possible for the phenyl radicals to be substituted, for example, by halogen, for example chlorine, lower alkoxy, for example methoxy, and/or by nitro.

A mercapto group can be protected, for example, by an optionally substituted alkyl group, an acyl group, a silyl group, or in the form of a thioacetal or a disulphide. Preferred protecting groups for mercapto are 1-phenyl-lower alkyl optionally substituted in the phenyl radical, for example, by methoxy or by nitro, for example benzyl, 4-methoxybenzyl, 2-nitrobenzyl, bis(4-methoxyphenyl)methyl or trityl, the acyl radicals of a carbonic acid semiester mentioned for amino groups, for example benzyloxycarbonyl, and also lower alkylaminocarbonyl, for example ethylaminocarbonyl, tri-lower alkylsilyl, for example trimethylsilyl, benzylthiomethyl, tetrahydropyranyl or lower alkylthio, for example methylthio, ethylthio or benzylthio.

A hydrocarbon radical $R^b$ or $R^c$ is, for example, a hydrocarbon radical mentioned under substituents of hydroxy or amino $R^3$, especially a lower alkyl radical having from 1 to 7 C-atoms, for example methyl, ethyl or tert.-butyl, or an aryl-lower alkyl radical having from 7 to 15 C-atoms, for example benzyl.

A silyl radical $R^b$ or $R^c$ is substituted by three identical or different hydrocarbon radicals as are mentioned above as substituents of hydroxy or amino $R^3$. Such a hydrocarbon radical is, for example, lower alkyl having from 1 to 7 C-atoms, for example methyl, ethyl, isopropyl, tert.-butyl or tert.-hexyl, monocyclic cycloalkyl having from 5 to 7 C-atoms, for example cyclohexyl, aryl having from 6 to 14 C-atoms, for example phenyl, or aryl-lower alkyl having from 7 to 20 C-atoms, for example benzyl or trityl. A silyl radical $R^b$ or $R^c$ is, for example, trimethylsilyl, triethylsilyl, tripropylsilyl, triisopropylsilyl, tributylsilyl, triphenylsilyl, dimethyl-tert.-butylsilyl, dimethylisopropylsilyl, dimethylphenylsilyl, diphenylmethylsilyl, diphenylisopropylsilyl, diphenyl-tert.-butylsilyl or dimethyltritylsilyl.

Salts of compounds of the formula I are, for example, acid addition salts of the amino group, for example with inorganic acids, for example hydrochloric acid, sulphuric acid, nitric acid or phosphoric acid, or with organic carboxylic or sulphonic acids, for example with acetic acid, chloroacetic acid, trichloroacetic acid, trifluoroacetic acid, propionic acid, glycolic acid, succinic acid, maleic acid, hydroxymaleic acid, methylmaleic acid, fumaric acid, malic acid, tartaric acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid, with methanesulphonic acid, trifluoromethanesulphonic acid, ethanesulphonic acid, 2-hydroxyethanesulphonic acid, ethane-1,2-disulphonic acid, benzenesulphonic acid, 4-methylbenzenesulphonic acid or naphthalene-2-sulphonic acid, or with other acidic organic compounds, such as ascorbic acid. Compounds of the formula I having acid groups, for example carboxy, can also form internal salts.

Compounds of the formula I in which $R^3$ represents hydroxy can also form alkali metal salts, for example sodium or potassium salts, or alkaline earth metal salts, for example magnesium or calcium salts, zinc salts, ammonium salts, salts with organic amines, for example with optionally substituted mono-, di- or tri-alkylamines, for example with cyclohexylamine, diethylamine, cyclohexylethylamine, dibutylamine, trimethylamine, triethylamine or tri-(2-hydroxyethyl)amine, or with tetra-substituted organic ammonium ions, for example with tetramethylammonium, tetraethylammonium or tetrabutylammonium.

Compounds of the formula I in which $R^3$ represents hydroxy can also form internal salts.

The compounds of the present invention can be converted in known manner into polypeptide-like compounds having useful physiological properties. For example, they can be condensed in the manner described in European Patent Applications 143 746 and 184 550 with carboxylic acids or carboxylic acid derivatives, thus producing blood pressure-reducing renin-inhibitors.

Renin passes from the kidneys into the blood where it brings about the cleavage of angiotensinogen to form the decapeptide angiotensin I which is then cleaved in the lungs, the kidneys and other organs to the octapeptide angiotensin II. The latter raises the blood pressure both directly through arterial constriction and indirectly by releasing from the adrenal glands the hormone aldosterone which retains sodium ions, which is associated with an increase in the extracellular fluid volume. This increase can be attributed to the action of angiotensin II itself or of the heptapeptide angiotensin III which is formed therefrom as a cleavage product. Inhibitors of the enzymatic activity of renin bring about a reduction in the formation of angiotensin I. As a consequence of this, a smaller quantity of angiotensin II is produced. The reduced concentration of that active peptide hormone is the direct cause of the blood pressure-reducing action of renin-inhibitors.

The action of renin-inhibitors is demonstrated inter alia experimentally in in vitro tests in which the reduction in the formation of angiotensin I is measured in various systems (human plasma, purified human renin together with synthetic or natural renin substrate). The renin-inhibitors that can be prepared from the compounds of the present invention exhibit inhibiting activity in the in vitro systems in concentrations of as low as approximately $10^{-6}$ to approximately $10^{-9}$ mol/liter.

The compounds of the present invention can also be converted in known manner into polypeptide-like compounds having analgesic activity, for example into compounds that inhibit the aminopeptidase which degrades encephalin.

The invention relates especially to processes for the preparation of compounds of the formula I, preferably in diastereoisomerically pure form, in which $R^1$ represents lower alkyl, hydroxy-lower alkyl, cycloalkyl, cycloalkyl-lower alkyl, aryl or aryl-lower alkyl, $R^2$ represents lower alkyl, hydroxy-lower alkyl, cycloalkyl, cycloalkyl-lower alkyl, aryl, aryl-lower alkyl, optionally substituted amino, optionally substituted hydroxy, optionally substituted mercapto, substituted sulphinyl or substituted sulphonyl, and $R^3$ represents optionally substituted amino, and of salts of these compounds.

The invention relates more especially to processes for the preparation of compounds of the formula I, preferably in diastereoisomerically pure form, in which $R^1$ represents lower alkyl, for example isopropyl or isobutyl, cycloalkyl, for example cyclohexyl, cycloalkyl-lower alkyl, for example cyclopentylmethyl, cyclohexylmethyl, 2-cyclohexylethyl or cycloheptylmethyl, phenyl or phenyl-lower alkyl, for example benzyl, $R^2$ represents lower alkyl, for example methyl, ethyl, n-propyl, isopropyl, n-butyl, sec.-butyl or isobutyl, hydroxy-lower alkyl, for example hydroxymethyl or 2-hydroxyethyl, cycloalkyl, for example cyclopentyl or cyclohexyl, cycloalkyl-lower alkyl, for example cyclohexylmethyl, phenyl, phenyl-lower alkyl, for example benzyl, amino, lower alkylamino, for example methylamino or ethylamino, di-lower alkylamino, for example dimethylamino, lower alkanoylamino, for example acetylamino or pivaloylamino, substituted amino as part of a ring, for example pyrrolidino, piperidino or morpholino, hydroxy, lower alkoxy, for example methoxy or ethoxy, lower alkanoyloxy, for example acetoxy, mercapto, lower alkylthio, for example methylthio, ethylthio or tert.-butylthio, or lower alkylsulphonyl, for example methylsulphonyl, ethylsulphonyl or tert.-butylsulphonyl, and $R^3$ represents substituted amino in which the substituent is optionally substituted alkyl having up to 12 C-atoms, for example lower alkyl, for example methyl, ethyl, n-butyl or n-pentyl, n-alkyl, for example n-octyl or n-decyl, hydroxy-lower alkyl, for example 2-hydroxyethyl, carboxy-lower alkyl, for example carboxymethyl, 1-carboxyethyl, 1-carboxyisobutyl or 3-carboxypropyl, optionally substituted carbamoyl-lower alkyl, for example carbamoylmethyl, 1-carbamoylethyl, 1-carbamoylisobutyl or 1-carboxy-lower alkyl in which the carboxy group is amidated by the amino function of a natural amino acid, a lower alkyl ester thereof or an amide thereof, for example 1(histindinylcarbonyl)-2-methyl-butyl, 1-(methoxyhistindinylcarbonyl)-2-methylbutyl or 1(amidohistindinylcarbonyl)-2-methyl-butyl, cycloalkyl, for example cyclohexyl, cycloalkyl-lower alkyl, for example cyclopropylmethyl or cyclohexylmethyl, lower alkenyl, for example allyl, lower alkynyl, for example 2-propynyl, aryl, for example phenyl, aryl-lower alkyl, for example benzyl, heteroaryl, for example 2-pyridyl or 3-indolyl, or heteroaryl-lower alkyl containing a mono- or bi-cyclic heterocycle having one or two nitrogen atoms, for example 2- or 4-pyridylmethyl, 2-(2- or 4-pyridyl)-ethyl, 4-imidazolylmethyl, 2-(4-imidazolyl)-ethyl, 3-indolylmethyl or 2-(3-indolyl)-ethyl, or $R^3$ represents di-lower alkylamino, for example dimethylamino or diethylamino, or substituted amino as part of a ring, for example pyrrolidino, piperidino or morpholino, and of salts of such compounds.

The invention relates most especially to processes for the preparation of compounds of the formula I in which $R^1$ represents lower alkyl, for example isopropyl or isobutyl, cycloalkyl-lower alkyl, for example cyclopentylmethyl, cyclohexylmethyl, 2-cyclohexylethyl or cycloheptylmethyl, or phenyl-lower alkyl, for example benzyl, $R^2$ represents lower alkyl, for example methyl, ethyl, isopropyl or sec.-butyl, cycloalkyl, for example cyclopentyl or cyclohexyl, phenyl, di-lower alkylamino, for example dimethylamino, substituted amino as part of a five- or six-membered ring, for example pyrrolidino, piperidino or morpholino, lower alkoxy, for example methoxy or ethoxy, lower alkylthio, for example methylthio or ethylthio, or lower alkylsulphonyl, for example methylsulphonyl or ethylsulphonyl, and $R^3$ represents lower alkylamino, for example methyl-, ethyl-, n-butyl- or n-pentyl-amino, hydroxy-lower alkylamino, for example 2-hydroxyethylamino, carboxy-lower alkylamino, for example carboxymethyl-, 1-carboxyethyl-, 1-carboxyisobutyl- or 3-carboxypropyl-amino, carbamoyl-lower alkylamino, for example carbamoylmethyl-, 1-carbamoylethyl- or 1-carbamoylisobutyl-amino, cycloalkyl-lower alkylamino, for example cyclopropylmethylamino, aryl-lower alkylamino, for example benzylamino, heteroaryl-lower alkylamino containing a mono- or bi-cyclic heterocycle having one or two nitrogen atoms, for example 2- or 4-pyridylmethylamino, 2-(2- or 4-pyridyl)-ethylamino, 4-imidazolylmethylamino, 2-(4-imidazolyl)-ethylamino, 3-indolylmethylamino or 2-(3-indolyl)-ethylamino, di-lower alkylamino, for example dimethylamino or diethylamino, or substituted amino as part of a five- or six-membered ring, for example pyrrolidino, piperidino or morpholino, and the C-atoms carrying the radicals $R^1$ and OH both have the R-configuration or both have the S-configuration, preferably the S-configuration, and the C-atom carrying the radical $R^2$ has the R- or S-configuration, and of salts of such compounds.

The invention relates above all to processes for the preparation of compounds of the formula I in which $R^1$ represents lower alkyl, for example isobutyl, or cycloalkyl-lower alkyl, for example cyclopentylmethyl, cyclohexylmethyl, 2-cyclohexylethyl or cycloheptylmethyl, $R^2$ represents lower alkyl, for example isopropyl, di-lower alkylamino, for example dimethylamino, or lower alkoxy, for example methoxy, and $R^3$ represents lower alkylamino, for example methylamino or n-butylamino, and the C-atoms carrying the radicals $R^1$ and OH have the S-configuration and the C-atom carrying the radical $R^2$ has the R- or S-configuration, and of salts of such compounds.

The invention relates first and foremost to a process for the preparation of the compounds mentioned in the Examples.

PROCESSES

Conversion of a compound of the formula II into a compound of the formula V:

The esterification of an allyl alcohol of the formula II with an acid of the formula II in which $R^b$ represents hydrogen, to form an allyl ester of the formula

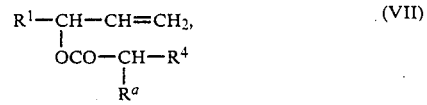

in which $R^1$, $R^4$ and $R^a$ have the meanings mentioned, can be effected by one of the customary esterification methods, for example in the presence of an acid catalyst, for example a proton-containing acid, for example sulphuric acid, hydrochloric acid or hydrobromic acid, phosphoric acid or a strong organic acid, such as an arylsulphonic acid, for example p-toluenesulphonic acid, or an alkylsulphonic acid, for example methane- or trifluoromethane-sulphonic acid, a proton-free Lewis acid catalyst, for example boron trifluoride etherate, or anhydrous zinc salts, for example zinc chloride, or strongly acidic ion-exchangers, for example ion-exchangers having sulphonic acid groups, without solvent, for example in an excess of the alcohol of the formula II, or in the presence of an inert solvent, for example toluene, chlorobenzene, cyclohexane or the like, at temperatures of from 0° to 200° C., preferably from 50° to 150° C., for example at the boiling point of the solvent. The water of reaction produced during the esterification is preferably removed, for example by azeotropic distillation with suitable entrainer solvents, for example toluene, by adsorption on molecular sieve, for example molecular sieve 3A, or by reaction with thionyl chloride, or the like.

Suitable acid derivatives for the esterification of an allyl alcohol are, for example, anhydrides, for example the anhydride with hydrochloric acid (COCl in place of $COOR^b$), anhydrides with strong organic acids, for example with trifluoroacetic acid, with formic acid or with a sulphonic acid, for example p-toluenesulphonic acid, or anhydrides with themselves. Such anhydrides can be prepared by known methods, for example also in situ by the addition of trifluoroacetic acid anhydride or p-toluenesulphonic acid chloride in an excess of pyridine. Acid anhydrides are reacted with allyl alcohols in the presence of one of the acid catalysts mentioned above or in the presence of a base, for example an organic tertiary amine, for example triethylamine, dimethylaniline, pyridine or 4-dimethylaminopyridine. Instead of a base, the allyl alcohol of the formula II can also be used in the form of an alcoholate, for example prepared with sodium hydride or potassium hydride. The reaction conditions and solvents mentioned above and also dipolar aprotic solvents, for example acetonitrile or dimethylformamide, and temperatures of from −30° to 50° C., for example around 0° C., are suitable.

The esterification of an allyl alcohol of the formula II with an ester of the formula III in which $R^b$ represents a hydrocarbon radical or a silyl radical is effected according to one of the customary transesterification methods, for example in the presence of an acid catalyst as is mentioned above in the esterification of the acid or in the presence of a base, for example in the presence of a catalytic amount of the alcoholate which has been produced from the allyl alcohol of the formula II and sodium hydride or potassium hydride or sodium in metallic form. Preferably, the reaction is carried out in an excess of the alcohol of the formula II that is to be introduced and/or the resulting alcohol of the formula $R^bOH$ is removed, for example by distillation or adsorption on molecular sieve, for example molecular sieve 4A.

Most especially preferred is the transesterification in the presence of a tetraalkoxy derivative of titanium or zirconium, for example in the presence of titanium tetraethoxide, titanium tetrabutoxide or titanium tetraisopropoxide, preferably titanium tetraethoxide. The catalyst is added in amounts of from 0.01% to 50%, for example from 1% to 30%, and the transesterification is carried out at temperatures of from 50° to 200° C., for example at the boiling point of the alcohol $R^bOH$ or of an inert solvent that has been added, for example toluene or cyclohexane.

The esterification of the allyl alcohol of the formula II with an ester derivative of the formula III includes, for example, the reaction with an orthoester of the formula III in which the group $COOR^b$ has been replaced by a radical $C(OR^b)_3$ and $R^b$ represents lower alkyl, for example methyl or ethyl, the reaction with a dialkoxyethylene of the formula III in which the group $CH\!\!=\!\!COOR^b$ has been replaced by a radical $C\!\!=\!\!C(OR^b)_2$ and $R^b$ represents lower alkyl, for example ethyl, and the reaction with the corresponding dialkylamino derivatives in which one radical $OR^b$ in each case has been replaced by $NR_2^b$. The esterification with an orthoester or a dialkoxyethylene is advantageously effected in the presence of an acid catalyst as is mentioned above, for example boron trifluoride etherate, or with a weakly acidic catalyst, for example a lower alkanecarboxylic acid, for example acetic acid or propionic acid, or an arylcarboxylic acid, for example benzoic acid or 2,4,6-trimethylbenzoic acid, without solvent or in one of the mentioned inert solvents at temperatures of from 0° to 200° C., for example from 0° to 100° C.

If the radicals $R^1$ and $R^4$ contain sensitive functional groups, for example carboxy, amino, hydroxy or mercapto groups, these groups in compounds of the formula II and/or III are preferably protected by one of the above-mentioned protecting groups before the esterification.

The rearrangement of the allyl ester of the formula VII produced from the compounds of the formulae II and III, to form a compound of the formula IV takes place, depending on the nature of the substituents $R^1$, $R^4$ and $R^a$, in situ under the reaction conditions chosen for the esterification or transesterification.

If, for example, $R^1$ is phenyl, $R^4$ is hydrogen, $R^a$ is a radical $COOR^b$ and $R^b$ is ethyl and if sodium acetate is used as transesterification catalyst, it is known that heating to 200°–230° C. initiates the transesterification reaction and decarboxylation to form the compound of the formula IV. The resulting product, however, is obtained, after hydrolysis of the ester function, in a yield of only 51% in impure form. Surprisingly, it has now been found that if the transesterification of compounds of the formula III in which $R^a$ is a group $COOR^b$ and $R^4$ also may be other than hydrogen is carried out with an allyl alcohol of the formula II in the presence of a titanium or zirconium tetraalcoholate, the ester of the formula VII can be converted directly into a compound of the formula IV in which $R^a$ represents hydrogen and $R^c$ has the same meaning as $R^b$ under mild conditions and with substantially higher yields than before. For example, in the reaction of compounds of the formula II with compounds of the formula III in which $R^a$ is a group $COOR^b$ and $R^b$ is lower alkyl, for example ethyl, in the presence of from 1% to 30% of a titanium tetra-lower alkoxide, for example titanium tetraethoxide, at temperatures of from 150° to 220° C. without solvent or in an inert solvent, for example mesitylene, decahydronaphthalene or dichlorobenzene, compounds of the formula IV in which $R^a$ is hydrogen and $R^c$ is lower alkyl as in $R^b$ are produced in yields of from 50% to approaching 100%.

If the esterification of the allyl alcohol of the formula II with an orthoester derivative of the formula III in which the group COOR$^b$ has been replaced by a radical C(OR$^b$)$_3$, R$^b$ represents lower alkyl, for example methyl or ethyl, and R$^a$ represents hydrogen, is effected in the presence of a weakly acidic organic compound, for example a lower alkanecarboxylic acid, such as propionic acid, the rearrangement to form a compound of the formula IV in which R$^a$ is hydrogen and R$^c$ is lower alkyl as in R$^b$ already takes place under the reaction conditions of the esterification, for example at temperatures of from 100° to 150° C. without solvent or in the presence of an inert solvent.

Similarly, the rearrangement to form a compound of the formula IV in which R$^a$ is a group COOR$^b$ and R$^c$ is lower alkyl as in R$^b$ takes place if the esterification with a dialkoxyethylene of the formula III in which the group CH—COOR$^b$ has been replaced by a radical C=C(OR$^b$)$_2$ and R$^a$ represents a group COOR$^b$ and R$^b$ represents lower alkyl, is carried out in the presence of one of the weakly acidic organic catalysts mentioned above, at temperatures of from 100° to 160° C.

If the esterification of the allyl alcohol of the formula II is effected with an ester derivative of the formula III in which the group CH—COOR$^b$ has been replaced by a radical C=C(OR$^b$)(NR$_2^b$), then a compound of the formula IV in which the radical COOR$^c$ has been replaced by a group CONR$_2^b$ is produced without the addition of a catalyst by reacting at temperatures of from 100° to 200° C., preferably from 130° to 170° C., for example in an inert solvent, for example xylene or dimethylformamide.

The rearrangement of allyl esters of the formula VII preliminarily formed from compounds of the formulae II and III, in a separate reaction step is the normal case unless one of the above-mentioned ester derivatives of the formula III is used for esterification and R$^a$ is hydrogen. For rearrangement, the allyl ester of the formula VII is deprotonated with a strong, non-nucleophilic base at low temperatures, for example from −100° to 0° C., preferably from −80° to −30° C., in a polar aprotic solvent or solvent mixture, for example a polar ether, for example tetrahydrofuran, dimethoxyethane or diethylene glycol dimethyl ether, optionally mixed with an amide, for example dimethylformamide, N-methylpyrrolidone or hexamethylphosphoric acid triamide, or a urea, for example N,N'-dimethyl-N,N'-propylene urea, and/or an inert hydrocarbon, for example hexane or toluene, and, if desired, is treated with a silylating agent, and is rearranged by heating to temperatures of from −20° to 80° C., preferably from 0° to 30° C., to form a salt of the compound of the formula IV in which R$^c$ represents hydrogen, or to form a compound of the formula IV in which R$^c$ represents the silyl radical used in the silylation.

Non-nucleophilic bases are compounds that remove a hydrogen from the α-position in esters without adding to the carbonyl group of the ester function. Examples of such strong, non-nucleophilic bases are alkali metal salts, for example lithium, potassium or sodium salts, of secondary amines having hydrocarbon radicals of large spatial volume or silyl radicals, for example lithium diisopropylamide, lithium dicyclohexylamide, lithium isopropylcyclohexylamide, lithium bis(trimethylsilyl)amide, potassium bis(trimethylsilyl)amide, lithium 2,2,6,6-tetramethylpiperide or the like.

Preferred silylating agents are tri-lower alkylsilyl halides having identical or different silyl radicals, for example trimethylsilyl chloride, tert.-butyldimethylsilyl chloride or triisopropylsilyl chloride.

The compounds of the formula IV prepared by one of the reaction steps mentioned above usually have an E-configured C=C double bond.

In esters of the formula VII in which R$^1$ is other than hydrogen and other than vinyl, the carbon atom carrying the radical R$^1$ is chiral. If an enantiomeric form of the ester of the formula VII is used in the rearrangement reaction, the chirality of that carbon atom can be transferred to the carbon atom carrying the radical R$^4$ in the product of the formula IV if suitable reaction conditions are chosen. In so doing, it is possible to produce from the one enantiomeric form of the ester of the formula VII, by selecting suitable solvents or solvent mixtures in the rearrangement reaction, the one or the other enantiomeric form of the product of the formula IV.

Compounds of the formula IV in which R$^c$ represents a silyl radical are hydrolysed by water and/or a lower alkanol, preferably methanol, at temperatures of from 0° to 50° C. If R$^c$ represents a hydrocarbon radical, the ester is converted into the acid of the formula V by one of the customary standard methods of ester hydrolysis, for example in the presence of aqueous acid or aqueous base, for example aqueous-alcoholic potassium hydroxide solution or sodium hydroxide solution. If R$^a$ is a group COOR$^b$ and R$^b$ is other than hydrogen, then, following the above-mentioned ester hydrolysis, the reaction product is heated at temperatures of from 50° to 200° C., preferably around 150° C., in order to split off the carbon dioxide. If the compound of the formula IV contains optionally protected functional groups in the radical(s) R$^1$ and/or R$^4$, then, depending on the nature of the protecting group, these functional groups are freed again under the conditions of the ester hydrolysis.

If R$^4$ represents halogen, this radical is exchanged after or, preferably, before any hydrolysis and/or decarboxylation for a radical R$^2$ representing amino, hydroxy or mercapto. The exchange takes place under the customary conditions of a nucleophilic substitution of a halide. The introduction of an amino group, for example dimethylamino, diethylamino or pyrrolidino, can be achieved by reaction with the corresponding free amine in an inert, preferably polar, solvent, for example an alcohol, for example methanol or ethanol, acetonitrile, tetrahydrofuran, dimethylformamide, dimethyl sulphoxide or the like, at temperatures of from 0° to 100° C. To introduce an unsubstituted amino group, the reagents and conditions mentioned hereinafter for the conversion of a compound of the formula VI into a compound of the formula I are preferably used. Halogen can be exchanged for unsubstituted hydroxy under the above-mentioned conditions of the ester hydrolysis. Etherified hydroxy, for example methoxy, is introduced by reaction in an excess of the corresponding alcohol, and acylated hydroxy, for example acetoxy, by reaction in an excess of the corresponding carboxylic acid, the reactions preferably being carried out in the presence of a non-nucleophilic base in order to bind the hydrogen halide liberated. A substituted, for example etherified, mercapto group is introduced by reaction with the corresponding mercaptan or alkali metal mercaptide in one of the above-mentioned, inert, polar solvents and at the stated temperatures.

The exchange of halogen for one of the mentioned radicals R$^2$ can generally be carried out such that the configuration of the carbon atom carrying the radical R$^4$ or R$^2$ in compounds of the formula IV or V, respectively, inverts.

If $R^2$ is other than hydrogen and other than the radical of the formula $R^1CH=CHCH_2—$, then the compound of the formula V is chiral. If, in an end product of the formula I, the carbon atom carrying the radical $R^2$ is to have only one of the two possible configurations, then a racemic compound of the formula V is subjected, preferably at this stage, to separation of the enantiomers. Separations of enantiomers of racemic carboxylic acids of the formula V are achieved analogously to known methods, for example by fractional crystallisation or chromatographic separation of diastereoisomeric carboxylic acid salts or carboxylic acid amides with chiral, if desired enantiomerically pure, organic amines. For example, carboxylic acids of the formula V are reacted in a solvent with equimolar amounts of an enantiomerically pure amime, for example (R)- or (S)-α-phenylethylamine, (R)- or (S)-1-α- or β-naphthylethylamine, quinine, quinchonidine, dehydroabietylamine or d- or l-ephedrine, the diastereoisomeric salts are separated and purified by fractional crystallisation, the diastereoisomerically pure salts are cleaved by adding an aqueous acid, the amine used as adjunct is removed and the enantiomerically pure acid of the formula V is isolated. Conversion of a compound of the formula V into a compound of the formula VI:

The γ,δ-unsaturated carboxylic acids of the formula V are converted by halogenating agents into halolactones of the formula VI. Compounds of the formula VI in which X represents iodine are obtained, for example, by reacting acids of the formula V with iodine in aqueous or organic solvents, for example in water, aqueous lower alkanol, for example aqueous methanol or ethanol, in water/ether mixtures, for example water/diethyl ether, in acetonitrile, amides, for example dimethylformamide or N-methylpyrrolidone, polar ethers, for example tetrahydrofuran, dioxan or dimethoxyethane, or in halogenated hydrocarbons, for example methylene chloride or chloroform, at temperatures of from −80° to 50° C., preferably from 0° to 30° C., if desired in the presence of a base that binds hydriodic acid which is liberated, for example an alkali metal hydrogen carbonate, for example sodium hydrogen carbonate, or an alkali metal or alkaline earth metal carbonate, for example magnesium or calcium carbonate, and/or in the presence of potassium iodide which increases the solubility of iodine in aqueous solvents. Instead of iodine, another reagent that yields positive iodine can be used, for example N-iodosuccinimide or N-iodoacetamide.

Compounds of the formula VI in which X represents bromine are obtained by reacting acids of the formula V with bromine, N-bromosuccinimide or other reagents that yield positive bromine, in the above-mentioned solvents and under the mentioned reaction conditions, for example with bromine in aqueous sodium hydrogen carbonate solution containing, if desired, potassium bromide, with bromine in acetonitrile or with N-bromosuccinimide in dimethylformamide, tetrahydrofuran or the like. Compounds of the formula VI in which X represents chlorine are obtained in corresponding manner by using N-chlorosuccinimide as halogenating agent.

The configuration of the carbon atom carrying the radical $R^2$ influences the spatial arrangement of the substituents —OCO and —X in compounds of the formula VI. Under the customary reaction conditions of the halolactonisation, the two diastereoisomers that are produced by anti-periplanar addition of the substituents —OCO and —X to the double bond of the unsaturated acid of the formula V are preferentially formed. As a result of addition to an E-configured C=C double bond of the compound of the formula V the newly formed chiral carbon atoms thus have the R,S- or the S,R-configuration. Depending on the nature of the substituent $R^2$ and on the chosen reaction conditions, it is possible to carry out the reaction such that one of the those two diastereoisomers clearly predominates and can readily be isolated in pure form.

The carboxylic acid of the formula V is preferably converted into an amide or a hydroxamic acid ester of the formula

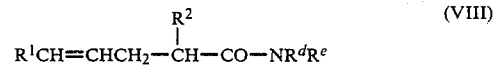

$$R^1CH=CHCH_2-\overset{R^2}{\underset{|}{CH}}-CO-NR^dR^e \quad (VIII)$$

before the treatment with the halogenating agent.

There are suitable, for example, amides of the formula VIII in which $R^d$ and $R^e$ each represents, independently of the other, lower alkyl, for example methyl or ethyl, cycloalkyl, for example cyclohexyl, or aryl-lower alkyl, for example benzyl, or $R^d$ and $R^e$ together represent lower alkylene, oxa-lower alkylene or lower alkylaza-lower alkylene having from 4 to 6 atoms in the chain, but with oxa or aza not being in the 1-position, for example 1,4-butylene, 1,5-pentylene, 1,6-hexylene, 3-oxa-1,5-pentylene or 3-methyl-3-aza-1,5-pentylene.

Such amides are prepared by the customary methods from the corresponding carboxylic acids of the formula V, as is described, for example, in "Methoden der organischen Chemie (Houben-Weyl)", volume E5, Thieme Verlag, Stuttgart 1985, pages 941–982. For example, the carboxylic acids are converted into the corresponding acid halide with a customary halogenating agent, for example thionyl chloride, phosphorus tri- or pentachloride, phosgene or oxalyl chloride, optionally in the presence of a catalyst, for example zinc chloride, pyridine, dimethylformamide or hexamethylphosphoric acid triamide, without solvent or in an inert solvent, for example a hydrocarbon, for example toluene or hexane, or an ether, for example diethyl ether, at temperatures of from 20° to 120° C., and are reacted with the corresponding amine, for example the di-lower alkylamine or the cyclic secondary amine, optionally in an inert organic solvent, for example a halogenated hydrocarbon, for example methylene chloride, or an ether, for example diethyl ether, and in the presence of a base, for example a trialkylamine, for example triethylamine or triisopropylamine, pyridine and/or 4-dimethylaminopyridine, at temperatures of from −30° to 100° C., for example around 0° C.

The amides of the formula VIII in which $R^d$ and $R^e$ have the meanings mentioned are subjected to halolactonisation under the reaction conditions mentioned for the carboxylic acids of the formula V. Halogenating agents that can be used for this are, for example, iodine, N-iodosuccinimide, bromine, N-bromosuccinimide or N-chlorosuccinimide in the mentioned solvents or solvent mixtures at temperatures of from −30° to 80° C., preferably from 0° to 30° C.

Especially preferred is the halolactonisation of amides of the formula VIII with N-bromosuccinimide in the presence of a weak acid, for example a lower alkanecarboxylic acid, for example acetic acid, in an aqueous-organic solvent mixture, for example aqueous tetrahydrofuran, at temperatures around 0° C. Under these preferred reaction conditions, of the possible diastereoisomers, there are predominantly formed only those diastereoisomers in which the radicals $R^2$ and the methyl group carrying the radicals $R^1$ and X are arranged trans to each other (with respect to the lactone ring) and the substituents —X and —OCO have been introduced by anti-periplanar addition to the double bond.

Hydroxamic acid esters suitable for the halolactonisation are compounds of the formula VIII in which $R^d$ represents lower alkyl, for example methyl or ethyl, and $R^e$ represents lower alkoxy, for example methoxy or ethoxy, or $R^d$ and $R^e$ together represent 1-oxa-lower alkylene having from 4 to 6 atoms in the chain, for example 1-oxa-1,4-butylene or 1-oxa-1,5-pentylene. Such hydroxamic acid esters are prepared by the customary methods from carboxylic acids of the formula V, as is described, for example, in "Houben-Weyl", Vol. E5, pages 1144–1149, for example by reacting a carboxylic acid halide, for example the carboxylic acid chloride, with an N,O-di-lower alkylhydroxylamine or the corresponding cyclic hydroxylamine, optionally in an inert organic solvent and in the presence of a base, for example under the reaction conditions customary for the preparation of di-lower alkylamides from carboxylic acid chlorides.

Hydroxamic acid esters of the formula VIII in which $R^d$ represents lower alkyl and $R^e$ represents lower alkoxy or $R^d$ and $R^e$ together represent 1-oxa-lower alkylene are preferably reacted with N-bromosuccinimide in one of the above-mentioned solvents or solvent mixtures at temperatures of from $-20°$ to $80°$ C., preferably around $0°$ C. In so doing, the same diastereoisomer of the formula VI as is also produced in the preferred cyclisation of carboxylic acid amides is preferentially formed.

If the radicals $R^1$ and $R^2$ contain sensitive functional groups, for example carboxy, amino, hydroxy or mercapto groups, in unprotected form, these groups in compounds of the formula V are preferably protected before the halolactonisation and, optionally, before the conversion into an amide or a hydroxamic acid ester of the formula VIII, by one of the protecting groups mentioned hereinbefore.

Conversion of a compound of the formula VI into a compound of the formula I:

In compounds of the formula VI, X representing halogen, especially chlorine, bromine or iodine, is exchanged for a radical bonded by way of nitrogen. This exchange is effected, for example, by a nucleophilic substitution using a suitable nitrogen-containing reagent, for example an azide, a cyanate, readily cleavable secondary amines, for example dibenzylamine, bis(phenylthio)amine or bis(trimethylsilyl)amine, readily cleavable tertiary amines, for example hexamethylenetetramine, imides, for example phthalimide or N-ethoxycarbonyl-p-toluenesulphonamide, hydrazines, for example N,N-dimethylhydrazine, cyanamide, guanidine or the like.

For example, in compounds of the formula VI in which X represents chlorine, bromine or iodine, X is exchanged for an azide according to the customary methods of a nucleophilic substitution, for example using an alkali metal azide, for example sodium azide, or ammonium azide, for example unsubstituted ammonium azide or tetrabutylammonium azide, in a polar organic solvent, for example in a lower alkanol, for example methanol or ethanol, in a di-lower alkyl ketone, for example acetone, a nitrile, for example acetonitrile, an amide, for example dimethylformamide, N,N-dimethylacetamide, N-methylpyrrolidone or hexamethylphosphoric acid triamide, a urea, for example N,N'-dimethyl-N,N'-propylene urea, a polar ether, for example tetrahydrofuran, dioxan, dimethoxyethane or diethylene glycol dimethyl ether, a lower alkoxy-lower alkanol, for example diethylene glycol monomethyl or monobutyl ether, dimethyl sulphoxide or mixtures of the mentioned solvents with one another or with water, at temperatures of from $0°$ to $200°$ C., preferably from $20°$ to $50°$ C. The exchange of halogen X for azide can also be achieved in two-phase systems, preferably in the presence of a phase-transfer catalyst, for example in water/halogenated hydrocarbon mixtures, for example water/chloroform or water/methylene chloride, or in water/hydrocarbon mixtures, for example water/toluene, for example with the addition of a benzyl tri-lower alkylammonium salt, for example benzyl trimethylammonium chloride or hydrogen sulphate, or of a long-chain alkyl-tri-lower alkyl-ammonium or -phosphonium salt, for example hexadecyltrimethylammonium or -phosphonium chloride, at temperatures of from $0°$ to $100°$ C., preferably from $20°$ to $80°$ C.

For the exchange of the radical X representing halogen for cyanate there are used, for example, alkali metal cyanate, for example potassium cyanate or sodium cyanate, or ammonium cyanate, for example tetrabutylammonium cyanate, in one of the above-mentioned polar aprotic solvents, for example in acetonitrile, dimethylformamide, N-methylpyrrolidone, tetrahydrofuran, dimethoxyethane, dimethyl sulphoxide or the like, at the temperatures mentioned. The exchange is also possible with silver cyanate in non-polar solvents, for example benzene or toluene, at temperatures of from $-20°$ to $50°$ C., for example around $0°$ C.

Under the same conditions as those of azide or cyanate it is also possible to introduce other salt-type nitrogen nucleophiles, for example the potassium salt of phthalimide or sodium or potassium N-ethoxycarbonyl-p-toluenesulphonamide.

The mentioned polar solvents and reaction temperatures are suitable also for the introduction of the other nitrogen nucleophiles mentioned, for example dibenzylamine or N,N-dimethylhydrazine. Depending on the nature of the substituents $R^1$ and $R^2$, however, the exchange must be carried out under conditions which are controlled in such a manner that the carbonyl group of the lactone ring is not at the same time reacted with the nitrogen-containing nucleophilic reagent, forming an open-chain acid derivative.

As a result of the above-described conversion of the compound of the formula VI in which X represents a halide into a compound of the formula VI in which X represents a nitrogen-containing radical, for example an azide, the configuration at the carbon atom carrying the substituent X inverts. If, for example, a diastereoisomer in which the carbon atom carrying the radical X has the R-configuration is used as starting material, the resulting azide or cyanate, for example, exhibits the S-configuration at that carbon atom, the configuration at the other chiral centres, especially at the carbon atom that carries the radical —OCO, and at the carbon atom that carries the radical $R^2$, remaining unchanged.

A lactone of the formula VI in which X represents azide, which has been prepared in the manner described above is either first reacted with a compound that introduces the radical $R^3$, forming a compound of the formula

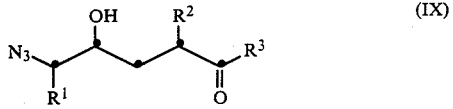
(IX)

or first treated with a reducing agent, producing a compound of the formula VI in which X represents amino.

If $R^3$ represents unsubstituted or substituted amino, the lactone of the formula VI in which X represents azide is preferably converted into an open-chain compound of the formula IX.

If $R^3$ is amino, the reagent is, for example, ammonia, for example gaseous ammonia or ammonia in concentrated or dilute aqueous solution. The reaction with ammmonia is carried out preferably at temperatures of from $-30°$ to $30°$ C., preferably around $0°$ C.

If $R^3$ is monosubstituted amino, the reagent is preferably the corresponding primary amine. The reaction can be carried out without solvent or in a polar solvent, for example in a lower alkanol, for example methanol or ethanol, or polar ether, for example tetrahydrofuran or dioxan, a nitrile, for example acetonitrile, or in another of the polar solvents mentioned above in the conversion into an azide, also in mixtures of the solvents with one another or with water. The opening of the lactone ring with a primary amine is carried out at temperatures of from $-30°$ to $100°$ C., preferably from $20°$ to $80°$ C.

If $R^3$ is disubstituted or cyclic amino, the reagent is the corresponding secondary amine. In this case, the same reaction conditions as in the case of primary amines are used.

If $R^3$ is optionally substituted hydroxy, the opening of the lactone ring of the formula VI in which X represents azide is possible with the reagents mentioned hereinafter which introduce the radical $R^3$ but is of little practical use since, at the same time, the azide group is partly or completely eliminated.

If the radical $R^3$ contains sensitive functional groups, for example carboxy, amino, hydroxy or mercapto groups, these groups in the reagent are advantageously protected by one of the protecting groups mentioned hereinbefore, before the reaction with compounds of the formula VI.

In the next reaction step, the azide radical in a compound of the formula IX is converted by reduction into an amino group. The reduction is preferably achieved by catalytic hydrogenation with hydrogen, for example in the presence of a noble metal catalyst, such as platinum, for example in the form of platinum oxide, finely divided metallic platinum, or metallic platinum supported on a carrier, palladium, for example in the form of metallic palladium on a carrier, for example on activated carbon, or also in the presence of activated nickel, for example Raney nickel. The catalytic hydrogenation is preferably carried out in an inert solvent or solvent mixture, for example in a halogenated hydrocarbon, for example methylene chloride, an ether, for example tetrahydrofuran or dioxan, an ester, for example ethyl acetate, an alcohol, for example methanol or ethanol, or mixtures of the mentioned solvents with one another or with water, at temperatures of from $0°$ to $50°$ C., for example from $20°$ to $30°$ C. The azide group can be converted into the amino group also with other reducing agents, for example with metallic zinc in the presence of an acid, with lithium aluminium hydride, also with triphenylphosphine or triethyl phosphite and subsequent acid treatment.

If a compound of the formula IX contains functional groups protected by protecting groups, then, depending on the nature of the protecting group and depending on the reaction conditions, these groups can be freed during the reduction of the azide group in the formula IX.

The lactone of the formula VI in which X represents azide can be converted according to the invention also into a lactone of the formula VI in which X represents amino and, after protecting the amino function, opened with a reagent that introduces the radical $R^3$.

For the reduction of the azide radical in a lactone of the formula VI the conditions mentioned above for the reduction of the azide radical in a compound of the formula IX are suitable.

The amino group in a lactone of the formula VI reduced in that manner is preferably protected by a protecting group before the introduction of the radical $R^3$. Suitable amino-protecting groups and conditions for their introduction are mentioned hereinbefore. The protecting groups used are preferably those which are stable under the conditions of the lactone ring opening, especially in the presence of a base, for example optionally substituted lower alkanoyl, optionally substituted benzoyl or arylmethyl, for example trityl.

If $R^3$ is unsubstituted or substituted amino, the lactone of the formula VI in which X represents optionally protected amino is converted with one of the reagents mentioned above, under the reaction conditions mentioned, into a compound of the formula I that is optionally protected at the amino function.

If $R^3$ is hydroxy, the opening of the lactone ring is carried out with an aqueous base, for example an alkali metal hydroxide or alkaline earth metal hydroxide, for example lithium, sodium or potassium hydroxide or calcium hydroxide, or a tetra-substituted ammonium hydroxide, for example benzyltrimethylammonium hydroxide, in aqueous solution at temperatures of from $0°$ to $100°$ C., for example from $20°$ to $50°$ C.

If $R^3$ is substituted hydroxy, the reagent is, for example, the corresponding alcohol. The opening of the ring is in this case carried out in an excess of the corresponding alcohol without solvent or in the presence of one of the polar organic solvents mentioned in the conversion of the halolactone into an azide with the exception of the lower alkanols mentioned, at the stated temperatures, preferably in the presence of a catalytic or equimolar amount of the alcoholate corresponding to the reagent, for example the sodium, potassium or titanium tetra-alcoholate.

A lactone of the formula VI in which X represents cyanate, that has been prepared in the manner described hereinbefore is reacted preferably with an alcohol, for example benzyl alcohol, the alcohol being added to the carbonyl group of the cyanate group and a carbonic acid semiester-protected derivative of the compound of the formula VI in which X represents amino being produced. Such a protected compound is reacted as described above with a reagent that introduces the radical $R^3$ and thereby converted into a compound of the formula I that is protected at the amino function by the acyl radical of a carbonic acid semiester.

Lactones of the formula VI in which X represents a nitrogen-containing radical other than azide or cyanate are preferably reacted first in the manner described above with a reagent that introduces the radical $R^3$.

In the last step, the amino group is then freed from the nitrogen-containing radical. If that radical is dibenzylamino, hydrazino or N,N-dimethylhydrazino, freeing is carried out by catalytic hydrogenation, for example under conditions such as those mentioned above for the reduction of the azide radical. From phthalimido the amino group is freed preferably by hydrazinolysis. The cleavage of the bis(phenylthio)amino group, the bis(trimethylsilyl)amino group or of the ammonium salt formed with hexamethylenetetramine is effected, for example, with an acid, for example with an aqueous mineral acid, such as hydrochloric acid or sulphuric acid. Using an aqueous acid and/or base, the corresponding cyanamino, guanidino and ethoxycarbonyl-p-toluenesulphonamido groups are hydrolysed.

Subsequent operations:

In a compound of the formula I prepared according to the process described above or in any of the intermediates mentioned of the formulae IV, V, VI, VIII or IX, in which one or more functional groups are protected, these groups, for example carboxy, amino, hydroxy and/or mercapto groups, can be freed in a manner known per se, optionally in stages or simultaneously, by means of solvolysis, especially hydrolysis, optionally enzymatic hydrolysis, alcoholysis or acidolysis, or by means of reduction, especially hydrogenolysis or chemical reduction. The removal of the protecting groups is described in the standardworks mentioned hereinbefore.

For example, protected carboxy, for example tert.-lower alkoxycarbonyl, lower alkoxycarbonyl substituted in the 2-position by an organic silyl group or in the 1-position by lower alkoxy or by lower alkylthio, or optionally substituted diphenylmethoxycarbonyl, can be converted into free carboxy by treatment with a suitable acid, such as formic acid or trifluoroacetic acid, optionally with the addition of a nucleophilic compound, such as phenol or anisole. Optionally substituted benzyloxycarbonyl can be freed, for example, by means of hydrogenolysis, that is to say by treatment with hydrogen in the presence of a metallic hydrogenation catalyst, such as a palladium catalyst. Suitably substituted benzyloxycarbonyl, such as 4-nitrobenzyloxycarbonyl, can be converted into free carboxy also by reduction, for example by treatment with an alkali metal dithionite, for example sodium dithionite, or with a reducing metal, for example zinc, or a reducing metal salt, such as a chromium(II) salt, for example chromium(II) chloride, customarily in the presence of a hydrogen-yielding agent that together with the metal is capable of producing nascent hydrogen, such as an acid, especially a suitable carboxylic acid, for example a lower alkanecarboxylic acid which may, if desired, be substituted, for example acetic acid, formic acid, glycolic acid, diphenylglycolic acid, lactic acid, mandelic acid, 4-chloromandelic acid or tartaric acid, or an alcohol or thiol, it being preferable to add water. It is also possible to convert 2-halo-lower alkoxycarbonyl (optionally after converting a 2-bromo-lower alkoxycarbonyl group into a corresponding 2-iodo-lower alkoxycarbonyl group) or aroylmethoxycarbonyl into free carboxy by treatment with a reducing metal or a reducing metal salt, as described above. Aroylmethoxycarbonyl can be cleaved also by treatment with a nucleophilic, preferably salt-forming, reagent, such as sodium thiophenolate or sodium iodide. 2-Tri-lower alkylsilyl-lower alkoxycarbonyl can be converted into free carboxy also by treatment with a salt of hydrofluoric acid yielding the fluoride anion, such as an alkali metal fluoride, for example sodium or potassium fluoride, optionally in the presence of a macrocyclic polyether ("Crown ether"), or with a fluoride of an organic quaternary base, such as tetra-lower alkylammonium fluoride or benzyl tri-lower alkylammonium fluoride, for example tetraethylammonium fluoride or tetrabutylammonium fluoride, in the presence of an aprotic polar solvent, such ad dimethyl sulphoxide or N,N-dimethylacetamide. Esterified carboxy can also be cleaved enzymatically, for example esterified arginine or lysine, such as lysine methyl ester, by means of trypsin.

A protected amino group is freed in a manner known per se and in various ways depending on the nature of the protecting groups, preferably by solvolysis or reduction. 2-Halo-lower alkoxycarbonylamino (optionally after converting a 2-bromo-lower alkoxycarbonylamino group into a 2-iodo-lower alkoxycarbonylamino group), aroylmethoxycarbonylamino or 4-nitrobenzyloxycarbonylamino can be cleaved, for example, by treatment with a suitable reducing agent, such as zinc in the presence of a suitable carboxylic acid, for example aqueous acetic acid. Aroylmethoxycarbonylamino can be cleaved also by treatment with a nucleophilic, preferably salt-forming, reagent, such as sodium thiophenolate, and 4-nitrobenzyloxycarbonylamino can be cleaved also by treatment with an alkali metal dithionite, for example sodium dithionite. Optionally substituted diphenylmethoxycarbonylamino, tert.-lower alkoxycarbonylamino or 2-tri-lower alkylsilyl-lower alkoxycrbonylamino can be freed by treatment with a suitable acid, for example formic or trifluoroacetic acid, optionally substituted benzyloxycarbonylamino can be freed, for example, by means of hydrogenolysis, that is to say by treatment with hydrogen in the presence of a suitable hydrogenation catalyst, such as a palladium catalyst, and optionally substituted triarylmethylamino or formylamino can be freed, for example, by treatment with an acid, such as a mineral acid, for example hydrochloric acid, or an organic acid, for example formic, acetic or trifluoroacetic acid, optionally in the presence of water. An amino group protected by 2-haloacetyl, for example 2-chloroacetyl, can be freed by treatment with thiourea in the presence of a base or with a thiolate salt, for example an alkali metal thiolate of thiourea, and subsequent solvolysis, for example alcoholysis or hydrolysis, of the resulting condensation product. An amino group protected by 2-tri-lower alkysilyl-lower alkoxycarbonyl can be converted into a free amino group also by treatment with a salt of hydrofluoric acid yielding fluoride anions, as indicated above in connection with the freeing of a correspondingly protected carboxy group.

A hydroxy or mercapto group protected by a suitable acyl group or by optionally substituted 1-phenyl-lower alkyl is freed analogously to a correspondingly protected amino group. A hydroxy group protected by 2,2-dichloroacetyl is freed, for example, by basic hydrolysis, while a hydroxy or mercapto group protected by tert.-lower alkyl, silyl or by a 2-oxa- or 2-thia-aliphatic or a 2-oxa- or 2-thia-cycloaliphatic hydrocarbon radical is freed by acidolysis, for example by treatment with a mineral acid or a strong carboxylic acid, for example trifluoroacetic acid. A hydroxy or mercapto group protected by an organic silyl group can be freed also with a fluoride salt, as indicated above for the freeing of a correspondingly protected carboxy group. A mercapto group protected in the form of a disulphide, for example by lower alkylthio, is freed by reduction, for example with lithium aluminium hydride or sodium borohydride. Thioacetals can be cleaved with mercury salts, for example aqueous mercury acetate.

A compound of the formula I prepared by the process described above or any of the mentioned intermediates of the formulae IV, V, VI, VIII or IX can be converted into another compound of the formula I or into another corresponding intermediate of the formula IV, V, VI, VIII or IX.

For example, an amino, hydroxy or mercapto group $R^2$ or also a carboxy group in a carboxyalkyl radical, an amino group in an aminoalkyl radical or a hydroxy group in a hydroxyalkyl radical $R^1$, $R^2$, $R^3$ or $R^4$ can be alkylated with an alkylating agent. Suitable alkylating agents are, for example, alkyl halides, sulphonic acid esters, Meerwein salts or 1-substituted 3-aryltriazenes, and for methylations also diazomethane. An amino, hydroxy or mercapto group can also be acylated, for example under the reaction conditions described for the introduction of acyl protecting groups.

A substituted mercapto group $R^2$ or $R^4$ can also be oxidised to a sulphinyl or sulphonyl group, or a sulphinyl group $R^2$ or $R^4$ can be oxidised to a sulphonyl group. For these oxidations there are preferably used selective oxidising agents, for example aromatic or aliphatic peroxycarboxylic acids, for example m-chloroperbenzoic acid or peracetic acid, hydrogen peroxide, potassium peroxomonosulphate or tert.-butyl hypochlorite. It is similarly possible to convert a sulphonyl group or sulphinyl group $R^2$ or $R^4$ into a substituted mercapto group, for example using hydrides, for example diisobutyl aluminium hydride or sodium borohydride, catalytic hydrogen, boranes, for example dichloroborane, or the like.

Salts of compounds of the formula I or of the mentioned intermediates are obtained in customary manner, for example acid addition salts by treatment with an acid or a suitable anion-exchange reagent, it being preferable to use stoichiometric amounts or only a small excess of the salt-forming agent. Internal salts of compounds of the formula I that contain, for example, a free carboxy group can be formed, for example, by neturalising salts, such as acid addition salts, to the isoelectric point, for example with weak bases, or by treatment with ion-exchangers. Salts of compounds of the formula IV or V containing carboxy groups can be formed, for example, by treatment with metal compounds, such as alkali metal salts of suitable organic carboxylic acids, for example the sodium salt of 2-ethylhexanoic acid, or with inorganic alkali metal or alkaline earth metal salts, for example sodium hydrogen carbonate, or with ammonia or a suitable organic amine.

Salts can be converted into the free compounds in customary manner: metal and ammonium salts, for example, by treatment with suitable acids, and acid addition salts, for example, by treatment with a suitable basic agent.

Stereoisomeric mixtures, especially diastereoisomeric mixtures, can be separated into the individual isomers in a manner known per se, for example by fractional crystallisation, chromatography, etc..

Racemates can be resolved in a manner known per se, for example after converting the optical antipodes into diastereoisomeric salts, for example by reaction with chiral, if desired enantiomerically pure, carboxylic or sulphonic acids, analogously to the process described above for the separation of enantiomers of compounds of the formula V.

The process of the invention also includes those forms in which intermediates are isolated and the remaining process steps are carried out with them, in which starting materials and reagents are formed in situ and/or in which intermediates and end products are further processed without being isolated.

The invention relates especially also to the novel process steps mentioned hereinafter, under the stated preferred reaction conditions, as such or as part of a whole process for the preparation of compounds of the formula I.

Preference is given to a process for the preparation of compounds of the formula IV in which $R^1$ and $R^4$ have the meanings mentioned above and $R^a$ represents hydrogen and $R^c$ represents hydrogen or lower alkyl, characterised in that an allyl alcohol of the formula II is reacted with a malonic acid ester of the formula III in which $R^a$ represents a group $COOR^b$ and $R^b$ represents lower alkyl, for example ethyl, in the presence of a tetraalkoxy derivative of titanium or zirconium, at temperatures of from 150° to 250° C., and, if desired, the resulting compound of the formula IV in which $R^a$ represents hydrogen and $R^c$ represents lower alkyl is hydrolysed with an aqueous base.

Very special preference is given to the process mentioned using from 1% to 30% of a tetra-lower alkoxy derivative of titanium, for example titanium tetraethoxide.

Preference is also given to a process for the preparation of compounds of the formula VI in which X represents chlorine, bromine or iodine, characterised in that a compound of the formula VIII in which $R^1$ and $R^2$ have the meanings mentioned above, $R^d$ and $R^e$, each represents, independently of the other, lower alkyl, cycloalkyl or aryl-lower alkyl, or together represent lower alkylene, oxa-lower alkylene or lower alkylaza-lower alkylene having from 4 to 6 C-atoms in the chain, but with aza not being in the 1-position, or $R^d$ represents lower alkyl and $R^e$ represents lower alkoxy, is reacted with a halogenating agent, for example N-chlorosuccinimide, N-bromosuccinimide, iodine or N-iodosuccinimide, and, if $R^e$ is other than lower alkoxy and $R^d$ and $R^e$ together are other than 1-oxa-lower alkylene, in the presence of a weak acid, for example a lower alkanecarboxylic acid, in an inert organic solvent or in an organic or aqueous-organic solvent mixture, at temperatures of from $-20°$ to 80° C.

Very special preference is given to a process for the preparation of compounds of the formula VI in which X represents bromine, characterised in that a compound of the formula VIII in which $R^1$ and $R^2$ have the meanings mentioned above and $R^d$ and $R^e$ represent identical or different lower alkyl or together represent lower alkylene or oxa-lower alkylene having from 4 to 6 atoms in the chain is reacted with N-bromosuccinimide in the presence of a weak acid, for example a lower alkanecarboxylic acid, for example acetic acid, in an aqueous-organic solvent mixture, for example aqueous tetrahydrofuran, at temperatures around 0° C.

Preference is similarly given to a process for the preparation of compounds of the formula VI in which X represents bromine, characterised in that a compound of the formula VIII in which $R^1$ and $R^2$ have the meanings mentioned above, $R^d$ represents lower alkyl and $R^e$ represents lower alkoxy or $R^d$ and $R^e$ together represent 1-oxa-lower alkylene having from 4 to 6 atoms in the chain is reacted with N-bromosuccinimide in an aqueous-organic solvent mixture, for example aqueous tetrahydrofuran, at temperatures around 0° C.

In all of the processes mentioned, the starting materials used and the reaction conditions chosen are preferably such that the compounds listed at the beginning as being especially preferred are obtained.

Starting materials of the formula II are known or, if novel, can be prepared analogously to known processes, for example by Grignard addition of vinyl-magnesium bromide to an aldehyde of the formula $R^1CHO$ or by reducton of an ethynyl ketone $R^1COC≡CH$.

Acids and esters of the formula II are likewise known or can be manufactured according to known methods. If $R^a$ is a group $COOR^b$, the corresponding compounds of the formula III are obtained by reacting the unsubstituted malonic acid ester with an alkylating agent that introduces the radical $R^4$ or, if $R^4$ represents halogen, optionally substituted hydroxy or amino, with the corresponding halogenating, oxidising or aminating agent. By hydrolysis and decarboxylation there are obtained in known manner from malonic acidesters of the formula III in which $R^a$ is a group $COOR^b$ the corresponding acids or esters of the formula III in which $R^a$ represents hydrogen. If $R^4$ is halogen, optionally substituted hydroxy or amino, the corresponding compounds of the formula III in which $R^a$ is hydrogen are obtained by the customary methods for the manufacture of α-halo-, α-hydroxy- and α-amino-carboxylic acids and derivatives thereof.

In addition, the invention relates to the novel intermediates used in the described process, especially to the novel compounds of the formulae IV, V, VI, VIII and IX.

For example, the invention relates to compounds of the formula

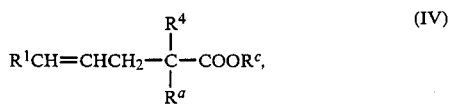

in which $R^1$ represents cycloalkyl-lower alkyl, $R^4$ represents optionally substituted alkyl, cycloalkyl, cycloalkyl-lower alkyl, aryl, aryl-lower alkyl, amino, hydroxy, mercapto, sulphinyl, sulphonyl, halogen or the radical of a natural amino acid apart from glycine, $R^a$ represents hydrogen and $R^c$ represents hydrogen, a hydrocarbon radical or a silyl radical, and salts of such compounds having salt-forming groups.

Preferred are compounds of the formula IV in which $R^1$ represents the radicals mentioned as being preferred under formula I and $R^4$ represents the radicals mentioned as being preferred for $R^2$ under formula I or represents halogen. Especially preferred are compounds of the formula IV in which $R^c$ represents hydrogen, compounds of the formula V, and also salts thereof, pure enantiomers and salts of pure enantiomers.

Salts of compounds of the formulae IV and V are, for example, the acid addition salts mentioned hereinbefore under formula I if $R^2$ or $R^4$ represents optionally substituted amino, also salts of the carboxy group in compounds of the formula IV in which $R^b$ and/or $R^c$ represent(s) hydrogen, for example as in compounds of the formula V, especially alkali metal salts, for example sodium or potassium salts, alkaline earth metal salts, for example magnesium or calcium salts, or zinc salts or optionally substituted ammonium salts, for example salts with organic amines, for example with the chiral amines mentioned hereinbefore that are suitable for resolving the racemates, or with achiral, optionally hydroxy-substituted mono-, di- or tri-alkylamines, for example with diethylamine, di-(2-hydroxyethyl)-amine, triethylamine, tris(hydroxmethyl)methylamine or tri-(2-hydroxyethyl)-amine, with cycloalkylamines, for example cyclohexylamine, dicyclohexylamine or ethylcyclohexylamine, or with aryl-lower alkylamines, for example with benzylamine, or also tetra-substituted organic ammonium salts, for example tetramethyl-, tetrabutyl- or benzyltrimethyl-ammonium salts.

The invention relates also to compounds of the formula

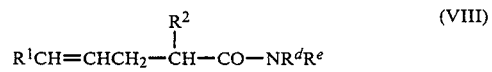

in which $R^1$ represents optionally substituted alkyl having 2 or more carbon atoms, cycloalkyl, cycloalkyl-lower alkyl, aryl, aryl-lower alkyl or the radical of a natural amino acid apart from glycine and alanine, $R^2$ represents optionally substituted alkyl, cycloalkyl, cycloalkyl-lower alkyl, aryl, aryl-lower alkyl, amino, hydroxy, mercapto, sulphinyl, sulphonyl or the radical of a natural amino acid apart from glycine, and $R^d$ and $R^e$ each represents, independently of the other, lower alkyl, cycloalkyl or aryl-lower alkyl, $R^d$ and $R^e$ together represent lower alkylene, oxa-lower alkylene or lower alkylaza-lower alkylene having from 4 to 6 C-atoms in the chain, but with aza not being in the 1-position, or $R^d$ represents lower alkyl and $R^e$ represents lower alkoxy, and salts of such compounds in which $R^2$ represents optionally substituted amino.

Preferred are compounds of the formula VIII in which $R^1$ and $R^2$ represent radicals mentioned as being preferred under formula I. Also preferred are compounds in which $R^d$ represents lower alkyl and $R^e$ represents lower alkyl or lower alkoxy or $R^d$ and $R^e$ together represent lower alkylene or oxa-lower alkylene having from 4 to 6 atoms in the chain, and pure enantiomers thereof.

Salts of compounds of the formula VIII in which $R^2$ represents optionally substituted amino are, for example, the acid addition salts mentioned hereinbefore under formula I.

The invention relates also to compounds of the formula

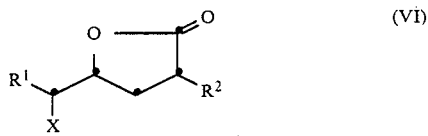

in which $R^1$ represents optionally substituted alkyl having 2 or more carbon atoms, cycloalkyl, cycloalkyl-lower alkyl, aryl, aryl-lowr alkyl or the radical of a natural amino acid apart from glycine and alanine, $R^2$ represents optionally substituted alkyl, cycloalkyl, cycloalkyl-lower alkyl, aryl, aryl-lower alkyl, amino, hydroxy, mercapto, sulphinyl, sulphonyl or the radical of a natural amino acid apart from glycine, and X represents chlorine, bromine, iodine, azide, cyanate or amino, and salts of such compounds having salt-forming groups.

Preferred are compounds of the formula VI in which $R^1$ and $R^2$ represent the radicals mentioned as being preferred under formula I, and also pure diastereoisomers or enantiomers of these compounds. Especially preferred are diastereoisomers of the mentioned compounds in which x represents chlorine, bromine or iodine, especially bromine, and the carbon atoms that carry the radicals X and —OCO have the R- and S-configuration or the S- and R-configuration, and also pure enantiomers of these diastereoisomers. Similarly preferred are diastereoisomers of the mentioned compounds in which X is azide and the carbon atoms that carry the radicals X and —OCO have the R- and R-configuration or the S- and S-configuration, and also pure enantiomers of these diastereoisomers.

Salts of compounds of the formula VI having salt-forming groups are, for example, the acid addition salts of compounds in which X represents amino and/or $R^2$ represents optionally substituted amino, which salts are mentioned hereinbefore under formula I.

The invention relates also to compounds of the formula

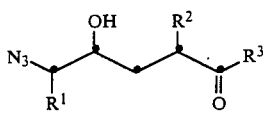 (IX)

in which $R^1$ represents hydrogen, optionally substituted alkyl, cycloalkyl, cycloalkyl-lower alkyl, aryl, aryl-lower akyl or the radical of a natural amino acid, $R^2$ represents hydrogen, optionally substituted alkyl, cycloalkyl, cycloalkyl-lower alkyl, aryl, aryl-lower alkyl, amino, hydroxy, mercapto, sulphinyl, sulphonyl or the radical of a natural amino acid, and $R^3$ represents optionally substituted amino, and salts of such compounds having salt-forming groups.

Preferred are compounds of the formula IX in which $R^1$, $R^2$ and $R^3$ represent the radicals mentioned as being preferred under formula I, and pure diastereoisomers or enantiomers of these compounds. Especially preferred are diastereoisomers of the mentioned compounds in which the carbon atoms that carry the radicals $N_3$ and OH have the R- and R-configuration or the S- and S-configuration, and also enantiomers in which these carbon atoms both have the S-configuration.

Salts of compounds of the formula IX having salt-forming groups are, for example, the acid addition salts of compounds in which $R^2$ is optionally substituted amino and/or in which the radical $R^3$ contains an amino group, which salts are mentioned hereinbefore under formula I.

The invention relates especially to the intermediates of the formulae IV, V, VI, VIII and IX mentioned in the Examples. invention, but do not limit the scope thereof in any way.

Temperatures are given in degrees Celsius. The values for proton nuclear resonance spectroscopy ($^1$H-NMR) are given in ppm (parts per million) based on tetramethylsilane ($\delta=0$) as the internal standard. s=singlet, d=doublet, t=triplet, q=quartet, m=multiplet, dd=double doublet. Coupling values J in Hertz (Hz). In elementary analyses, the empirical formula, the molecular weight and calculated (calc.) and found analysis values are given.

Optical rotations $[\alpha]_D$ are measured using the sodium D line, c=concentration (g/100 ml).

Abbreviations abs. absolute
ee enantiomeric excess
m.p. melting point
THF tetrahydrofuran
DMF dimethylformamide
HPLC high-pressure liquid chromatography

EXAMPLE 1

1-cyclohexyl-3-buten-2-ol

A solution of 60 g (0.47 mol) of cyclohexylacetaldehyde in 400 ml of abs. THF is added dropwise at $-20°$ to a solution of vinylmagnesium bromide in abs. THF, prepared from 13.8 g (0.57 mol) of magnesium and 66.3 g (0.62 mol) of vinyl bromide in 500 ml of abs. THF. When the addition is complete, the whole is stirred for 30 minutes at $-20°$ and then hydrolysed with 900 ml of saturated ammonium chloride solution. After diluting with 250 ml of $H_2O$, the reaction mixture is extracted three times with 1 liter of ether each time, washed three times with 500 ml of brine each time, dried with $MgSO_4$ and then concentrated by evaporation in a rotary evaporator. The residue is distilled at $50°/0.1$ mbar.

$C_{10}H_{18}O$ (154.25): calc. C 77.87 H 11.77%; found C 77.62 H 11.54%.

EXAMPLE 2

The following are prepared analogously to Example 1:

(a) 1-cyclopentyl-3-buten-2-ol from cyclopentylacetaldehyde.
$C_9H_{16}O$ (140.23): calc. C 77.09 H 11.50%; found C 76.97 H 11.24%;

(b) 1-cyclohexyl-4-penten-3-ol from 3-cyclohexylpropionaldehyde.
$C_{11}H_{20}O$ (168.28): calc. C 78.51 H 11.98%; found C 78.70 H 11.97%;

(c) 1-cycloheptyl-3-buten-2-ol from cycloheptylacetaldehyde.
$C_{11}H_{20}O$ (168.28): calc. C 78.51 H 11.98%; found C 78.06 H 11.92%;

(d) 5-methyl-1-hexen-3-ol from isovaleraldehyde.
$C_7H_{14}O$ (114.19): calc. C 73.63 H 12.36%; found C 73.79 H 12.57%.

EXAMPLE 3

6-cyclohexyl-2-isopropyl-4-hexenoic acid 23.15 g (0.15 mol) of 1-cyclohexyl-3-buten-2-ol, 6.85 g (0.03 mol) of tetraethyl orthotitanate and 61.5 ml (0.30 mol) of isopropylmalonic acid diethyl ester are placed in a flask and stirred for 1 hour at 170° and then for 24 hours at 200°. Excess malonic acid ester is distilled off at 20 mbar, and the residue is dissolved in 120 ml of ethanol and, after the addition of 120 ml of 6N KOH, stirred under reflux for 7 hours. After cooling, the reaction mixture is filtered and the filtrate is extensively concentrated by evaporation in a rotary evaporator. The aqueous phase is extracted once with ether, acidified to pH 1 with 6N HCl while cooling with ice and then extracted three times with ether. The combined organic phases are washed with brine, dried with $MgSO_4$ and concentrated by evaporation in a rotary evaporator. The residue is distilled at $137°-140°/0.025$ mbar.

$C_{15}H_{26}O_2$ (238.37): calc. C 75.58 H 11.00%; found C 75.49 H 10.91%.

$^1$H-NMR (CDCl$_3$): 5.28–5.55 (m, 2H, HC=CH).

The reaction can also be carried out with a smaller excess of isopropylmalonic acid ester (1.1 instead of 2 equivalents) and less tetraethyl orthotitanate (0.1 instead of 0.2 equivalents) without any substantial reduction in yield.

EXAMPLE 4

The following are manufactured analogously to Example 3:

(a) 6-cyclopentyl-2-isopropyl-4-hexenoic acid from 1-cyclopentyl-3-buten-2-ol and isopropylmalonic acid diethyl ester.

$C_{14}H_{24}O_2$ (224.34): calc. C 74.96 H 10.79%; found C 74.86 H 11.13%.

$^1$H-NMR (CDCl$_3$): 5.3–5.55 (m, 2H, HC=CH).

(b) 7-cyclohexyl-2-isopropyl-4-heptenoic acid from 1-cyclohexyl-4-penten-3-ol and isopropylmalonic acid diethyl ester.

$C_{16}H_{28}O_2$ (252.40): calc. C 76.14 H 11.18%; found C 76.24 H 11.23%.

$^1$H-NMR (CDCl$_3$): 5.3–5.5 (m, 2H, HC=CH).

(c) 6-cycloheptyl-2-isopropyl-4-hexenoic acid from 1-cycloheptyl-3-buten-2-ol and isopropylmalonic acid diethyl ester.

$C_{16}H_{28}O_2$ (252.40): calc. C 76.14 H 11.18%; found C 76.24 H 11.23%.

$^1$H-NMR (CDCl$_3$): 5.3–5.5 (m, 2H, HC=CH).

(d) 6-cyclohexyl-2-methoxy-4-hexenoic acid from 1-cyclopentyl-3-buten-2-ol and methoxymalonic acid diethyl ester.

$C_{13}H_{22}O_3$ (226.32): calc. C 68.99 H 9.80%; found C 68.80 H 9.99%.

$^1$H-NMR (CDCl$_3$): 5.33–5.61 (m, 2H, HC=CH); 3.85 (dd, 1H, CHOR); 3.47 (s, 3H, OCH$_3$).

(e) 6-cyclohexyl-2-dimethylamino-4-hexenoic acid ethyl ester from 1-cyclohexyl-3-buten-2-ol and dimethylaminomalonic acid diethyl ester, isolated in the form of the ester before the treatment with 6N KOH.

$^1$H-NMR (CDCl$_3$): 5.26–5.55 (m, 2H, HC=CH); 5.16 (q, 2H, OCH$_2$); 3.12 (dd, 1H, CHNR$_2$); 2.33 (s, 6H, NCH$_3$).

(f) 2-isopropyl-7-methyl-4-octenoic acid from 5-methyl-1-hexen-3-ol and isopropylmalonic acid diethyl ester.

$C_{12}H_{22}O_2$ (198.31): calc. C 72.63 H 11.18%; found C 72.43 H 11.02%.

$^1$H-NMR (CDCl$_3$): 5.16–5.45 (m, 2H, HC=CH).

(g) 6-cyclohexyl-2-phenyl-4-hexenoic acid ethyl ester from 1-cyclohexyl-3-buten-2-ol and phenylmalonic acid diethyl ester, isolated in the form of the ester before the treatment with 6N KOH.

$C_{20}H_{28}O_2$ (300.44): calc. C 79.96 H 9.40%; found C 80.00 H 9.56%.

$^1$H-NMR (CDCl$_3$): 5.3–5.5 (m, 2H, HC=CH).

(h) 6-cyclohexyl-2-methyl-4-hexenoic acid ethyl ester from 1-cyclohexyl-3-buten-2-ol and methylmalonic acid diethyl ester, isolated in the form of the ester before the treatment with 6N KOH.

$^1$H-NMR (CDCl$_3$): 2.38–2.51 (m, 1H, CHCOO); 5.3–5.5 (m, 2H, HC=CH).

(i) 2-bromo-6-cyclohexyl-4-hexenoic acid ethyl ester from 1-cyclohexyl-3-buten-2-ol and bromomalonic acid diethyl ester, isolated in the form of the ester before the treatment with 6N KOH.

$^1$H-NMR (CDCl$_3$): 4.1–4.25 (m, 3H, OCH$_2$ and CHBrCOO); 5.25–5.6 (m, 2H, HC=CH).

(j) 2-chloro-6-cyclohexyl-4-hexenoic acid ethyl ester from 1-cyclohexyl-3-buten-2-ol and chloromalonic acid diethyl ester, isolated in the form of the ester before the treatment with 6N KOH.

$^1$H-NMR (CDCl$_3$): 4.15–4.30 (m, 3H, OCH$_2$ and CHClCOO); 5.25–5.6 (m, 2H, HC=CH).

(k) 2-tert.-butyldimethylsilyloxy-6-cyclohexyl-4-hexenoic acid ethyl ester from 1-cyclohexyl-3-buten-2-ol and tert.-butyldimethylsilyloxymalonic acid diethyl ester, isolated in the form of the ester before the treatment with 6N KOH.

$^1$H-NMR (CDCl$_3$): 5.28–5.5 (m, 2H, HC=CH).

(l) 6-cyclohexyl-2-phenylthio-4-hexenoic acid ethyl ester from 1-cyclohexyl-3-buten-2-ol and phenylthiomalonic acid diethyl ester, isolated in the form of the ester before the treatment with 6N KOH.

$^1$H-NMR (CDCl$_3$): 3.65 (t J=6, 1H, CHCOO); 5.3–5.6 (m, 2H, HC=CH).

EXAMPLE 5

Isovaleric acid 1-cyclohexyl-3-buten-2-yl ester 2.4 ml (19.5 mmol) of isovaleric acid chloride are added dropwise at 0° C. to a solution of 2.75 g (17.76 mmol) of 1-cyclohexyl-3-buten-2-ol, 3 ml (21.3 mmol) of triethylamine and 430 mg (3.5 mmol) of 4-dimethylaminopyridine in 20 ml of methylene chloride. When the addition is complete, the mixture is stirred for a further 3 hours at room temperature. After diluting with ether, the mixture is washed twice with 2N HCl, twice with saturated NaHCO$_3$ solution and twice with brine and dried over MgSO$_4$. After concentration by evaporation, the residue is distilled in a bulb tube at 150°/0.007 mbar.

$^1$H-NMR (CDCl$_3$): 5.70–5.86 (m, 1H); 5.30–5.40 (m, 1H); 5.24 (d, 1H); 5.14 (d, 1H).

EXAMPLE 6

6-cyclohexyl-2-isopropyl-4-hexenoic acid (alternative methods of preparation)

(a) 1.4 ml (2.3 mmol) of 1.6N n-butyllithium in hexane are added dropwise at −20° to a solution of 0.39 ml (2.3 mmol) of cyclohexylisopropylamine in 4 ml of abs. THF. After 15 minutes at −20°, the mixture is cooled to −78° and 500 mg (2.1 mmol) of isovaleric acid 1-cyclohexyl-3-buten-2-yl ester in 1 ml of abs. THF are added dropwise. When the addition is complete, the mixture is heated to room temperature over a period of 1 hour and then stirred at that temperature for 2 hours. The reaction mixture is introduced into 5 ml of cold 1N NaOH and extracted twice with ether. The aqueous phase is acidified to pH 1 with concentrated HCl and extracted with ether. The organic phases are washed with brine, dried with MgSO$_4$ and concentrated by evaporation. The residue is distilled in a bulb tube at 150°/0.01 mbar and, as a result, yields a product that is identical with the compound of Example 3.

(b) To a solution, prepared as described in (a), of 6 mmol of lithium cyclohexylisopropylamide in abs. THF there are added dropwise, at −78°, first 2.3 ml (18 mmol) of trimethylchlorosilane and then 1.2 g (5 mmol) of isovaleric acid 1-cyclohexyl-3-buten-2-yl ester. The solution is maintained at −78° for 1 hour, heated to room temperature over a period of 1½ hours and stirred at that temperature for 1 hours. the reaction mixture is cooled to 0°, hydrolysed by adding 0.5 ml of methanol, diluted with ether, washed with 1N HCl and brine, dried over MgSO$_4$ and concentrated by evaporation in a rotary evaporator. The residue is distilled as described in (a) and yields the same product.

EXAMPLE 7

Enantioselective preparation of 6-cyclohexyl-2(S)-isopropyl-4-hexenoic acid (a) 1-cyclohexyl-3-butyn-2(S)-ol:

As directed by D. R. M. Walton and F. Waugh, J. Organomet. Chem. 37, 45 (1972), bis(trimethylsilyl)acetylene is acylated with cyclohexylacetic acid chloride and hydrolysed with aqueous/methanolic borax solution to 1-cyclohexyl-3-butyn-2-one. Reduction with (S)-B-(3-pinanyl)-9-borabicyclo[3.3.1]nonane ((S)-Alpine-Borane ®, Aldrich, 88% ee) as directed by M. M Midland et al., Tetrahedron 40, 1371 (1984) yields 1-cyclohexyl-3-butyn-2(S)-ol.

$C_{10}H_{16}O_2$ (152.24): calc. C 78.90 H 10.60% found C 78.73 H 10.83%.

$^1$H-NMR (CDCl$_3$): 0.83–2.0 (m, 14H); 2.45 (d J=2, 1H, HC≡C); 4.45 (dxt, J=8 and 2, 1H, CHO). $[\alpha]_D = -8.1°$ (c=0.9, CHCl$_3$). The enantiomeric excess is determined by $^1$H-NMR after derivatisation with the Mosher reagent R(+)-α-methoxy-α-trifluoromethylphenylacetic acid chloride and is 80% ee.

(b) Isovaleric acid 1-cyclohexyl-3-buten-2(S)-yl ester:

1-Cyclohexyl-3-butyn-2(S)-ol is reduced by partial hydrogenation in the presence of Lindlar catalyst to 1-cyclohexyl-3-buten-2(S)-ol and reacted analogously to Example 5 with isovaleric acid chloride.

$C_{15}H_{26}O_2$ (283.37): calc. C 75.58 H 11.00 O 13.43%; found C 75.40 H 11.26 O 13.41%.

$[\alpha]_D = -13.6°$ (c=1, CHCl$_3$), 80% ee.

(c) Rearrangement of the silyl enolate:

To a solution, prepared as described in Example 6a, of 6 mmol of lithium cyclohexylisopropylamide in abs. THF there are added dropwise, at −78°, first 2.3 ml (18 mmol) of trimethylchlorosilane and then 1.2 g (5 mmol) of isovaleric acid 1-cyclohexyl-3-buten-2(S)-yl ester. The solution is further processed as described in Example 6b. 6-cyclohexyl-2(S)-isopropyl-4-hexenoic acid of 78% ee is obtained.

EXAMPLE 8

6-cyclohexyl-2(R)- and 2(S)-isopropyl-4-hexenoic acid 154.65 g (0.65 mol) of racemic 6-cyclohexyl-2-isopropyl-4-hexenoic acid and 210.5 g (0.65 mol) of anhydrous quinine are dissolved in 1 liter of methanol. The mixture is concentrated by evaporation and the residue is recrystallised from ether hexane. The crystallisate is filtered with suction and thoroughly washed with cold hexane. The salt is treated with 1N HCl and the acid is extracted with ether. Concentration by evaporation yields 6-cyclohexyl-2(R)-isopropyl-4-hexenoic acid of 90% ee. If the quinine salt is recrystallised a second time from ether/hexane before the treatment with HCl, the (R)-acid obtainable therefrom has a purity of more than 95% ee.

The filtrate of the first crystallisation of the quinine salt is concentrated by evaporation and similarly treated with 1N HCl. The solution is extracted with ether and the extract concentrated by evaporation leaving 6-cyclohexyl-2(S)-isopropyl-4-hexenoic acid of 80% ee as residue. For further enrichment of the (S)-acid, an equimolar amount of (+)-dehydroabietylamine in methanol is added to that residue and the resulting mixture is concentrated by evaporation and recrystallised from methylene chloride/hexane. The crystallisate is treated with 1N HCl and the acid is extracted with ether. Concentration of the ether solution by evaporation yields the (S)-acid in a purity of 95% ee.

To determine the enantiomeric excess (ee), a sample of each acid is condensed with (+)-phenylethylamine in the presence of dicyclohexylcarbodiimide and 1-hydroxybenzotriazole and the ratio of the diastereoisomeric amides formed is determined by HPLC.

EXAMPLE 9

The following are prepared analogously to Example 8:

(a) 6-cyclopentyl-2(R) - and 2(S)-isopropyl-4-hexenoic acid (b) 7-cyclohexyl-2(R)- and 2(S)-isopropyl-4-heptenoic acid (c) 6-cycloheptyl-2(R)- and 2(S)-isopropyl-4-hexenoic acid

EXAMPLE 10

6-cyclohexyl-2(S)-isopropyl-4-hexenoic acid dimethylamide 42.6 ml (0.49 mol) of oxalyl chloride are metered into a solution of 58.1 g (0.244 mol) of 6-cyclohexyl-2(S)-isopropyl-4-hexenoic acid in 270 ml of abs. toluene and 0.5 ml of DMF. When the addition is complete, the reaction mixture is boiled under reflux for 90 minutes, then concentrated in a rotary evaporator. The residue is dissolved in 270 ml of dry CH$_2$Cl$_2$ and added dropwise, at 0°, to a solution of 17.2 g (0.38 mol) of dimethylamine and 61.4 ml (0.76 mol) of pyridine in 270 ml of CH$_2$Cl$_2$. After stirring for 30 minutes at 0°, the mixture is diluted with ether and washed twice with 2N HCl, twice with saturated NaHCO$_3$ solution and twice with brine. The combined organic phases are dried with MgSO$_4$ and concentrated by evaporation. The residue is distilled at 124°–128°/0.04 mbar.

$^1$H-NMR (CDCl$_3$): 5.21–5.50 (m, 2H, HC=CH); 3.04 (s, 3H, NCH$_3$); 2.95 (s, 3H, NCH$_3$).

EXAMPLE 11

The following are prepared analogously to Example 10:

(a) 6-cyclopentyl-2(S)-isopropyl-4-hexenoic acid dimethylamide $^1$H-NMR (CDCl$_3$): 5.25–5.50 (m, 2H, HC=CH); 3.03 (s, 3H, NCH$_3$); 2.96 (s, 3H, NCH$_3$).

(b) 7-cyclohexyl-2(S)-isopropyl-4-heptenoic acid dimethylamide $^1$H-NMR (CDCl$_3$): 5.25–5.50 (m, 2H, HC=CH); 3.03 (s, 3H, NCH$_3$); 2.96 (s, 3H, NCH$_3$).

(c) 6-cycloheptyl-2(S)-isopropyl-4-hexenoic acid dimethylamide $^1$H-NMR (CDCl$_3$): 5.25–5.50 (m, 2H, HC=CH); 3.05 (s, 3H, NCH$_3$); 2.96 (s, 3H, NCH$_3$).

(d) 6-cyclohexyl-2-methoxy-4-hexenoic acid dimethylamide $^1$N-NMR (CDCl$_3$): 5.33–5.58 (m, 2H, HC=CH); 5.03–5.1 (m, 1H, CHOR); 3.33 (s, 3H, OCH$_3$); 3.1 (s, 3H, NCH$_3$); 2.95 (s, 3H, NCH$_3$).

(e) 6-cyclohexyl-2-dimethylamino-4-hexenoic acid dimethylamide $^1$H-NMR (CDCl$_3$): 5.15–5.50 (m, 2H, HC=CH); 4.37–4.48 (m, 1H, CHNR$_2$); 3.1 (s, 3H, NCH$_3$); 2.95 (s, 3H, NCH$_3$); 2.2 (s, 6H, NCH$_3$).

(f) 2-isopropyl-7-methyl-4-octenoic acid dimethylamide

¹H-NMR (CDCl₃): 5.25–5.50 (m, 2h, HC=CH); 3.03 (s, 3H, NCH₃); 2.96 (s, 3H, NCH₃).

(g) 6-cyclohexyl-2(S)-isopropyl-4-hexenoic acid diethylamide

¹H-NMR (CDCl₃): 5.23–5.50 (m, 2H, HC=CH); 3.25–3.50 (m, 4H, NCH₂).

(h) 6-cyclohexyl-2(S)-isopropyl-4-hexenoic acid pyrrolidide

¹H-NMR (CDCl₃): 5.23–5.50 (m, 2H, HC=CH); 3.48 (t, 2H, NCH₂); 3.35 (t, 2H, NCH₂)

(i) 6-cyclohexyl-2(S)-isopropyl-4-hexenoic acid morpholide

¹H-NMR (CDCl₃): 5.20–5.50 (m, 2H, HC=CH); 3.50–3.72 (m, 8H, NCH₂CH₂O).

(j) 6-cyclohexyl-2(S)-isopropyl-4-hexenoic acid N-methoxy-N-methylamide

¹H-NMR (CDCl₃): 5.25–5.50 (m, 2H, HC=CH); 3.65 (s, 3H, OCH₃); 3.20 (s, 3H, NCH₃).

(k) 6-cyclohexyl-2(S)-isopropyl-4-hexenoic acid N-isopropyl-N-methoxyamide

¹H-NMR (CDCl₃): 5.25–5.50 (m, 2H, HC=CH); 4.55–4.70 (m, 1H, NCH); 3.75 (s, 3H, OCH₃).

(l) 6-cyclohexyl-2(S)-isopropyl-4-hexenoic acid N-isopropoxy-N-methylamide

¹H-NMR (CDCl₃): 5.25–5.50 (m, 2H, HC=CH); 4.0–4.2 (m, 1H, OCH); 3.2 (s, 3H, NCH₃).

(m) 6-cyclohexyl-2(S)-isopropyl-4-hexenoic acid tetrahydroisoxazolide

¹H-NMR (CDCl₃): 5.25–5.50 (m, 2H, HC=CH); 3.8–4.0 (m, 2H, OCH₂); 3.56–3.80 (m, 2H, NCH₂).

EXAMPLE 12

5(R)-bromo-6-cyclohexyl-2(S)-isopropyl-4(S)-hexanolide 88.5 g (0.5 mol) of N-bromosuccinimide and 30 g (0.5 mol) of glacial acetic acid in 1.1 liter of THF are added dropwise at 0°, over a period of 8 hours, to a solution of 60 g (0.23 mol) of 6-cyclohexyl-2(S)-isopropyl-4-hexenoic acid dimethylamide in 1.4 liters of THF/H₂O (2:1). When the addition is complete, the reaction mixture is stirred for 30 minutes at 0°, then poured onto 1.8 liters of ice-cold 40% sodium hydrogen sulphite solution. The aqueous phase is extracted three times with ether and the combined organic phases are washed in succession with 1N HCl, saturated NaHCO₃ solution and brine. After drying with MgSO₄ and evaporating off the solvent, the residue is chromatographed over silica gel with hexane/ether (2:1) and again concentrated. The residue is recrystallised from hexane, m.p. 95°–95.5°.

C₁₅H₂₅BrO₂ (317.27): calc. C 56.79 H 7.94 Br 25.19%; found C 56.94 H 8.04 Br 25.22%.

Instead of the dimethylamide, the diethylamide, pyrrolidide and morpholide are subjected to bromolactonisation in the same manner.

If hydroxamic acid esters, for example 6-cyclohexyl-2(S)-isopropyl-4-hexenoic acid N-methoxy-N-methylamide, the corresponding -N-isopropyl-N-methoxyamide, -N-isopropoxy-N-methylamide or -tetrahydroisoxazolide, are used, the bromolactonisation is carried out without glacial acetic acid.

EXAMPLE 13

The following are prepared analogously to Example 12:

(a) 5(R)-bromo-6-cyclopentyl-2(S)-isopropyl-4(S)-hexanolide m.p. 66°–68°

C₁₄H₂₃BrO₂ (303.24): calc. C 55.46 H 7.65 Br 26.35%; found C 55.81 H 7.48 Br 26.29%.

(b) 5(R)-bromo-7-cyclohexyl-2(S)-isopropyl-4(S)-heptanolide m.p. 64°–65°

C₁₆H₂₇BrO₂ (331.29): calc. C 58.01 H 8.22 Br 24.12%; found C 58.32 H 8.19 Br 24.03%.

(c) 5(R)-bromo-6-cycloheptyl-2(S)-isopropyl-4(S)-hexanolide m.p. 57°–58°

C₁₆H₂₇BrO₂ (331.29): calc. C 58.01 H 8.22 Br 24.12%; found C 57.99 H 8.17 Br 24.10%.

(d) rel(2R,4S,5R)-5-bromo-6-cyclohexyl-2-methoxy-4-hexanolide

¹H-NMR (CDCl₃): 4.57–4.65 (m, 1H); 4.17–4.23 (m, 1H); 4.06–4.10 (m, 1H); 3.57 (s, 3H, OCH₃).

(e) rel(2R,4S,5R)-5-bromo-6-cyclohexyl-2-dimethylamino-4-hexanolide

¹H-NMR (CDCl₃): 4.48–4.58 (m, 1H); 4.14–4.24 (m, 1H); 3.7 (t, 1H, CHNR₂); 2.4 (s, 6H, NCH₃).

(f) rel(2R,4R,5S)-5-bromo-2-isopropyl-7-methyl-4-octanolide

¹H-NMR (CDCl₃): 4.40–4.50 (m, 1H); 4.08–4.17 (m, 1H); 2.63–2.75 (m, 1H, CHCO).

EXAMPLE 14

5(S)-azido-6-cyclohexyl-2(S)-isopropyl-4(S)-hexanolide 42.5 g (0.135 mol) of 5(R)-bromo-6-cyclohexyl-2(S)-isopropyl-4(S)-hexanolide and 35 g (0.54 mol) of NaN₃ in 480 ml of N,N′-dimethyl-N,N′-propylene urea (DMPU) are stirred at room temperature for 72 hours and then poured onto 1 liter of ice-cold 0.1N HCl. The mixture is then extracted three times with ether, and the combined organic phases are washed twice with 0.1N HCl and three times with brine and dried with MgSO₄. After concentrating the solvent by evaporation, the residue is recrystallised from hexane: m.p. 38.5°–39°.

C₁₅H₂₅N₃O₂ (279.38): calc. C 64.49 H 9.02 N 15.04%; found C 64.53 H 8.96 N 15.04%.

EXAMPLE 15:

The following are prepared analogously to Example 14:

(a) 5(S)-azido-6-cyclopentyl-2(S)-isopropyl-4(S)-hexanolide, oil.

C₁₄H₂₃N₃O₂ (265.36): calc. C 63.37 H 8.74 N 15.84%; found C 63.36 H 8.92 N 15.59%.

(b) 5(S)-azido-7-cyclohexyl-2(S)-isopropyl-4(S)-heptanolide, oil.

C₁₆H₂₇N₃O₂ (293.41): calc. C 65.50 H 9.28 N 14.32%; found C 65.57 H 9.40 N 14.12%.

(c) 5(S)-azido-6-cycloheptyl-2(S)-isopropyl-4(S)-hexanolide, m.p. 48°–49°

C₁₆H₂₇N₃O₂ (293.41): calc. C 65.50 H 9.28 N 14.32%; found C 64.48 H 9.21 N 14.37%.

(d) rel(2R,4R,5R)-5-azido-2-isopropyl-7-methyl-4-octanolide, oil.

¹H-NMR (CDCl₃): 4.40–4.48 (m, 1H); 3.33–3.42 (m, 1H); 2.67–2.77 (m, 1H, CHCO).

EXAMPLE 16

5(S)-azido-6-cyclohexyl-4(S)-hydroxy-2(S)-isopropylhexanoic acid n-butylamide 24.9 g (0.09 mol) of 5(S)-azido-6-cyclohexyl-2(S)-isopropyl-4(S)-hexanolide in 250 ml of n-butylamine are boiled under reflux for 10 hours. After evaporating off the solvent, the residue is recrystallised from hexane: m.p. 100°–100.5°.

$C_{19}H_{36}N_4O_2$ (352.52): calc. C 64.74 H 10.29 N 15.89%; found C 65.06 H 10.40 N 15.89%.

EXAMPLE 17

The following are prepared analogously to Example 16:

(a) 5(S)-azido-6-cyclopentyl-4(S)-hydroxy-2(S)-isopropylhexanoic acid n-butylamide, m.p. 59°–61°.

$C_{18}H_{34}N_4O_2$ (338.50): calc. C 63.87 H 10.13 N 16.55%; found C 63.86 H 10.00 N 16.76%.

(b) 5(S)-azido-7-cyclohexyl-4(S)-hydroxy-2(S)-isopropylheptanoic acid n-butylamide, m.p. 99.5°–100°.

$C_{20}H_{38}N_4O_2$ (366.55): calc. C 65.53 H 10.45 N 15.28%; found C 65.72 H 10.46 N 15.28%.

(c) 5(S)-azido-6-cycloheptyl-4(S)-hydroxy-2(S)-isopropylhexanoic acid n-butylamide, m.p. 66.5°–67°.

$C_{20}H_{38}N_4O_2$ (366.55): calc. C 65.53 H 10.45 N 15.28%; found C 65.47 H 10.26 N 15.25%.

(d) 5(S)-azido-6-cyclohexyl-4(S)-hydroxy-2(S)-isopropylhexanoic acid methylamide from 5(S)-azido-6-cyclohexyl-2(S)-isopropyl-4(S)-hexanolide and methylamine in DMF at room temperature.

$^1$H-NMR (CDCl$_3$): 5.72 (q, 1H, NH); 3.42–3.52 (m, 1H); 3.23–3.32 (m, 1H); 2.83 (d, 3H, NCH$_3$).

EXAMPLE 18

5(S)-amino-6-cyclohexyl-4(S)-hydroxy-2(S)-isopropylhexanoic acid n-butylamide 21.3 g (0.06 mol) of 5(S)-azido-6-cyclohexyl-4(S)-hydroxy-2(S)-isopropylhexanoic acid n-butylamide in 240 ml of methanol are hydrogenated for 2 hours in the presence of 5 g of 10% palladium-on-carbon. The reaction mixture is filtered, concentrated in a rotary evaporator, and the residue is recrystallised from hexane: m.p. 88.5°–90°; $[\alpha]_D$ −27.2°±0.9° (c=1.1, CHCl$_3$).

$C_{19}H_{38}N_2O_2$ (326.53): calc. C 69.89 H 11.73 N 8.58%; found C 70.11 H 11.54 N 8.65%.

EXAMPLE 19

The following are prepared analogously to Example 18:

(a) 5(S)-amino-6-cyclopentyl-4(S)-hydroxy-2(S)-isopropylhexanoic acid n-butylamide, m.p. 93°–94°, $[\alpha]_D$ −23.8°±0.9° (c=1.1, CHCl$_3$).

$C_{18}H_{36}N_2O_2$ (312.50): calc. C 69.19 H 11.61 N 8.96%; found C 69.13 H 11.54 N 8.94%.

(b) 5(S)-amino-7-cyclohexyl-4(S)-hydroxy-2(S)-isopropylheptanoic acid n-butylamide, m.p. 90°–92°, $[\alpha]_D$ −18.5°±0.9° (c=1.1, CHCl$_3$).

$C_{20}H_{40}N_2O_2$ (340.55): calc. C 70.54 H 11.84 N 8.23%; found C 70.54 H 11.62 N 8.07%.

(c) 5(S)-amino-6-cycloheptyl-4(S)-hydroxy-2(S)-isopropylhexanoic acid n-butylamide, m.p. 81°–82°, $[\alpha]_D$ −25.4°±0.9° (c=1.1, CHCl$_3$).

$C_{20}H_{40}N_2O_2$ (340.55): calc. C 70.54 H 11.84 N 8.23%; found C 70.33 H 11.72 N 8.46%.

(d) 5(S)-amino-6-cyclohexyl-4(S)-hydroxy-2(S)-isopropylhexanoic acid methylamide, colourless oil, R$_f$ (methylene chloride/methanol/conc. ammonia 350:50:1)=0.11.

EXAMPLE 20

5(S)-benzyloxycarbonylamino-6-cyclohexyl-2(S)-isopropyl-4(S)-hexanolide 403 mg (1.44 mmol) of 5(S)-azido-6-cyclohexyl-2(S)-isopropyl-4(S)-hexanolide in 20 ml of methanol are hydrogenated in the presence of 200 mg of 10% palladium-on-carbon, a constant pH of 4 being maintained by the addition of 1N HCl. The catalyst is filtered off and washed with methanol, and the filtrate is concentrated by evaporation in a rotary evaporator. The resulting residue is placed in 10 ml of ethyl acetate at 0° and there is added thereto first 3.60 ml of 1M NaHCO$_3$ solution and then 0.59 ml of a solution of chloroformic acid benzyl ester 50% in toluene. When the addition is complete, the mixture is stirred at 0° for a further 15 minutes, then extracted twice with ethyl acetate. The combined organic phases are washed with brine, dried with MgSO$_4$ and concentrated by evaporation in a rotary evaporator. The residue is recrystallised from ethyl acetate/hexane:

m.p. 167.5°–168°; $[\alpha]_D$ −31.4°±0.9° (c=1, CHCl$_3$).

$C_{23}H_{33}NO_4$ (387.52): calc. C 71.29 H 8.58 N 3.61%; found C 71.56 H 8.64 N 3.52%.

We claim:

1. A process for the preparation of a compound of the formula

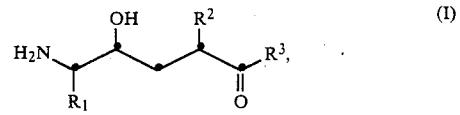

in which

R$^1$ represents hydrogen, alkyl, hydroxyalkyl, etherified hydroxyalkyl, esterified hydroxyalkyl, haloalkyl, carboxyalkyl, esterified carboxyalkyl, amidated carboxyalkyl, cyanoalkyl, aminoalkyl, mono- or di-lower alkylaminoalkyl, pyrrolidinoalkyl, piperidinoalkyl, morpholinoalkyl, oxoalkyl, cycloalkyl, cycloalkyl-lower alkyl, aryl, aryl-lower alkyl, 2-methylthioethyl, mercaptomethyl, 3-indolylmethyl, 4-imidazolylmethyl or 3-guanidinopropyl;

R$^2$ represents hydrogen, alkyl, hydroxyalkyl, etherified hydroxyalkyl, esterified hydroxyalkyl, haloalkyl, carboxyalkyl, esterified carboxyalkyl, amidated carboxyalkyl, cyanoalkyl, aminoalkyl, mono- or di-lower alkylaminoalkyl, pyrrolidinoalkyl, piperidinoalkyl, morpholinoalkyl, oxoalkyl, cycloalkyl, cycloalkyl-lower alkyl, aryl, aryl-lower alkyl, amino, mono- or di-lower alkylamino, aryl-lower alkylamino, lower alkanoylamino, lower alkoxycarbonylamino, aryl-lower alkoxycarbonylamino, pyrrolidino, piperidino, morpholino, hydroxy, lower alkoxy, lower alkanoyloxy-lower alkoxy, lower alkoxycarbonyloxy-lower alkoxy, aryloxy, aryl-lower alkoxy, lower alkanoyloxy, cycloalkylcarbonyloxy, arylcarbonyloxy, tri-lower alkylsilyloxy, mercapto, lower alkylthio, hydroxy-lower alkylthio, arylthio, aryl-lower alkylthio, lower alkanoylthio, lower alkylsulfinyl, hydroxy-lower alkylsufinyl, arylsulfinyl, aryl-lower alkylsulfinyl, lower alkylsulfonyl, hydroxy-lower alkylsulfonyl, arylsulfonyl, aryl-lower alkylsulfonyl, 2-methylthioethyl, mercaptomethyl, 3-indolylmethyl, 4-imidazolylmethyl or 3-guanidinopropyl; and R³ represents hydroxy, amino, substituted oxy or mono- or disubstituted amino wherein the substituent is alkyl, hydroxyalkyl, etherified hydroxyalkyl, esterified hydroxyalkyl, haloalkyl, carboxyalkyl, esterified carboxyalkyl, amidated carboxyalkyl, cyanoalkyl, aminoalkyl, mono- or di-lower alkylaminoalkyl, pyrrolidinoalkyl, piperidinoalkyl, morpholinoalkyl, oxoalkyl, cycloalkyl, cycloalkyl-lower alkyl, alkenyl, carboxyalkenyl, alkynyl, aryl, aryl-lower alkyl, heteroaryl or heteroaryl-lower alkyl, wherein heteroaryl contains one or two nitrogen atoms, an oxygen atom, a sulfur atom, one or two nitrogen atoms and an oxygen atom, or one or two nitrogen atoms and a sulfur atom, and wherein heteroaryl may be partially saturated, or R³ represents cyclic alkyleneamino, oxaalkyleneamino, thiaalkyleneamino or azaalkyleneamino wherein the aza nitrogen atom is unsubstituted or substituted by lower alkyl, phenyl, phenyl-lower alkyl, lower alkanoyl, lower alkoxycarbonyl or phenyl-lower alkoxycarbonyl, and of salts of such a compound, comprising the steps of: esterifying an allyl alcohol of the formula

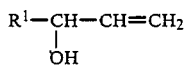
(II)

in the presence of a catalyst with an acid or ester of the formula

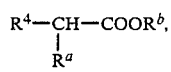
(III)

in which $R^a$ represents hydrogen or a group $COOR^b$ and $R^b$ represents hydrogen, lower alkyl, aryl-lower alkyl or tri-substituted silyl wherein the substituents are lower alkyl, cycloalkyl, aryl or aryl-lower alkyl, and $R^4$ has the meanings of $R^2$ or is halogen, or with a derivative of the compound of formula III wherein the group $COOR^b$ is replaced by a radical $C(OR^b)_3$ and $R^b$ represents lower alkyl, or wherein the group $CH-COOR^b$ is replaced by a radical $C=C(OR^b)_2$ and $R^b$ represents lower alkyl, or wherein one radical $OR^b$ in $COOR^b$, $C(OR^b)_3$ or $C=C(OR^b)_2$ is replaced by $NR_2^b$;
arranging the resulting compound in situ by heating or by treatment with a base and a silylating agent followed by heating;
hydrolyzing the resulting compound of the formula

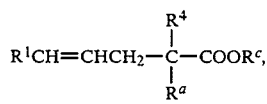
(IV)

in which $R^c$ represents hydrogen, lower alkyl, aryl-lower alkyl or tri-substituted silyl wherein the substituents are lower alkyl, cycloalkyl, aryl or aryl-lower alkyl, if $R^c$ is other than hydrogen or $R^a$ represents a group $COOR^b$ and $R^b$ is other than hydrogen, and decarboxylating if $R^a$ is a group $COOR^b$, and, if $R^4$ represents halogen, treating with a reagent which exchanges halogen for a radical $R^2$ as defined above;
haloactonizing the resulting compound of the formula

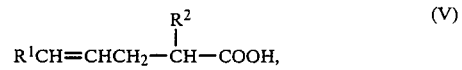
(V)

a carboxamide or a hydroxamic acid ester thereof, with a halogenating agent;
treating the resulting compound of the formula

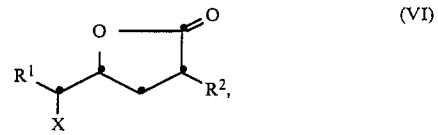
(VI)

in which X represents halogen, with a reagent which exchanges halogen for azido, isocyanato, readily cleavable secondary or tertiary amino or imido, hydrazino, cynamino or guanidino;
and, in the resulting compound, opening the lactone ring with a compound that introduces a radical R³, and converting the nitrogen-containing radical X into an amino group.

2. The process according to claim 1 for the preparation of a compound of the formula I in which R¹ represents lower alkyl, hydroxy-lower alkyl, cycloalkyl, cycloalkyl-lower alkyl, aryl or aryl-lower alkyl, R² represents lower alkyl, hydroxy-lower alkyl, cycloalkyl, cycloalkyl-lower alkyl, aryl, aryl-lower alkyl, amino, mono- or di-lower alkylamino, aryl-lower alkylamino, lower alkanoylamino, lower alkoxycarbonylamino, aryl-lower alkoxycarbonylamino, pyrrolidino, piperidino, morpholino, hydroxy, lower alkoxy, lower alkanoyloxy-lower alkoxy, lower alkoxycarbonyloxy-lower alkoxy, aryloxy, aryl-lower alkoxy, lower alkanoyloxy, cycloalkylcarbonyloxy, arylcarbonyloxy, tri-lower alkylsilyloxy, mercapto, lower alkylthio, hydroxy-lower alkylthio, arylthio, aryl-lower alkylthio, lower alkanoylthio, lower alkylsulfinyl, hydroxy-lower alkylsufinyl, arylsulfinyl, aryl-lower alkylsulfinyl, lower alkylsulfonyl, hydroxy-lower alkylsulfonyl, arylsulfonyl, aryl-lower alkylsulfonyl, and R³ represents amino or mono- or disubstituted amino wherein the substituent is alkyl, hydroxyalkyl, etherified hydroxyalkyl, esterified hydroxyalkyl, haloalkyl, carboxyalkyl, esterified carboxyalkyl, amidated carboxyalkyl, cyanoalkyl, aminoalkyl, mono- or di-lower alkylaminoalkyl, pyrrolidinoalkyl, piperidinoalkyl, morpholinoalkyl, oxoalkyl, cycloalkyl, cycloalkyl-lower alkyl, alkenyl, carboxyalkenyl, alkynyl, aryl, aryl-lower alkyl, heteroaryl or heteroaryl-lower alkyl, wherein heteroaryl contains one or two nitrogen atoms, an oxygen atom, a sulfur atom, one or two nitrogen atoms and an oxygen atom, or one or two nitrogen atoms and a sulfur atom, and wherein heteroaryl may be partially saturated, or R³ represents cyclic alkyleneamino, oxaalkyleneamino, thiaalkyleneamino or azaalkyleneamino wherein the aza nitrogen atom is unsubstituted or substituted by lower alkyl, phenyl, phenyl-lower alkyl, lower alkanoyl, lower alkoxycarbonyl or phenyl-lower alkoxycarbonyl, and of salts of such a compound.

3. The process according to claim 1 for the preparation of a compound of the formula I in which R¹ represents lower alkyl, cycloalkyl, cycloalkyl-lower alkyl, phenyl or phenyl-lower alkyl, $R^2$ represents lower alkyl, hydroxy-lower alkyl, cycloalkyl, cycloalkyl-lower alkyl, phenyl, phenyl-lower alkyl, amino, lower alkylamino, di-lower alkylamino, lower alkanoylamino, pyrrolidino, piperidino, morpholino, hydroxy, lower alkoxy, lower alkanoyloxy, mercapto, lower alkylthio or lower alkylsulfonyl, and $R^3$ represents substituted amino wherein the substituent is alkyl having up to 12 C-atoms, hydroxy-lower alkyl, carboxy-lower alkyl, amidated carboxy-lower alkyl, cycloalkyl, cycloalkyl-lower alkyl, lower alkenyl, lower alkynyl, aryl, aryl-lower alkyl, heteroaryl or heteroaryl-lower alkyl, wherein heteroaryl is mono- or bicyclic and contains one or two nitrogen atoms, or $R^3$ represents di-lower alkylamino, cyclic alkyleneamino, oxaalkyleneamino, thiaalkyleneamino or azaalkyleneamino wherein the aza nitrogen atom is unsubstituted or substituted by lower alkyl, phenyl, phenyl-lower alkyl, lower alkanoyl, lower alkoxycarbonyl or phenyl-lower alkoxycarbonyl, and of salts of such a compound.

4. The process according to claim 1 for the preparation of a compound of the formula I in which $R^1$ represents lower alkyl, cycloalkyl-lower alkyl or phenyl-lower alkyl, $R^2$ represents lower alkyl, cycloalkyl, phenyl, di-lower alkylamino, pyrrolidino, piperidino, morpholino, lower alkoxy, lower alkylthio or lower alkylsulfonyl, and $R^3$ represents lower alkylamino, hydroxy-lower alkylamino, carboxy-lower alkylamino, carbamoyl-lower alkylamino, cycloalkyl-lower alkylamino, aryl-lower alkylamino, heteroaryl-lower alkylamino wherein heteroaryl is mono- or bicyclic and contains one or two nitrogen atoms, di-lower alkylamino, pyrrolidino, piperidino or morpholino, and the C-atoms carrying the radicals $R^1$ and OH both have the R-configuration or both have the S-configuration and the C-atom carrying the radical $R^2$ has the R- or S-configuration, and of salts of such a compound.

5. Process according to claim 1 for the preparation of compounds of the formula I in which $R^1$ represents lower alkyl or cycloalkyl-lower alkyl, $R^2$ represents lower alkyl, di-lower alkylamino or lower alkoxy, and $R^3$ represents lower alkylamino, and the C-atoms carrying the radicals $R^1$ and OH have the S-configuration and the C-atom carrying the radical $R^2$ has the R- or S-configuration, and of salts of such compounds.

6. Process according to claim 1 for the preparation of the compound of the formula I in which $R^1$ represents cyclohexylmethyl, $R^2$ represents isopropyl and $R^3$ represents n-butylamino and the C-atoms carrying the radicals $R^1$, $R^2$ and OH have the S-configuration.

* * * * *